US009501887B2

(12) United States Patent
Berg et al.

(10) Patent No.: US 9,501,887 B2
(45) Date of Patent: Nov. 22, 2016

(54) OBJECT DISPENSER HAVING A VARIABLE ORIFICE AND IMAGE IDENTIFICATION

(71) Applicant: PHARMADVA, LLC, Honeoye Falls, NY (US)

(72) Inventors: Michel J. Berg, Rochester, NY (US); Jeffrey C. Robertson, Rochester, NY (US); Lowell A. Onderdonk, Canandaigua, NY (US); Joel M. Reiser, Mendon, NY (US); Kenneth D. Corby, Rochester, NY (US)

(73) Assignee: Pharmadva, LLC, Honeoye Falls, NY (US)

( * ) Notice: Subject to any disclaimer, the term of this patent is extended or adjusted under 35 U.S.C. 154(b) by 437 days.

(21) Appl. No.: 13/948,385

(22) Filed: Jul. 23, 2013

(65) Prior Publication Data
US 2014/0025199 A1    Jan. 23, 2014

Related U.S. Application Data

(60) Provisional application No. 61/674,561, filed on Jul. 23, 2012.

(51) Int. Cl.
| | |
|---|---|
| *G07F 11/00* | (2006.01) |
| *G07F 17/00* | (2006.01) |
| *A61J 7/00* | (2006.01) |
| *G06F 19/00* | (2011.01) |

(52) U.S. Cl.
CPC ............ *G07F 11/005* (2013.01); *A61J 7/0084* (2013.01); *G06F 19/30* (2013.01); *G07F 17/0092* (2013.01)

(58) Field of Classification Search
USPC .......................................... 211/211; 700/232
See application file for complete search history.

(56) References Cited

U.S. PATENT DOCUMENTS 5,405,048 A * 4/1995 Rogers ................ B65G 1/1373
                                                    221/1
5,502,944 A    4/1996 Kraft et al.
(Continued)

FOREIGN PATENT DOCUMENTS

| AU | WO 2010059569 A2 * | 5/2010 | ........... G01N 35/025 |
|---|---|---|---|
| DE | GB 1153041 A * | 5/1969 | ............... B61G 5/06 |
| WO | WO-2006102409 | 9/2006 | |

OTHER PUBLICATIONS

PCT International Search Report, for co-pending related Application No. PCT/US2013/051620; Dec. 31, 2013.
(Continued)

*Primary Examiner* — Gene Crawford
*Assistant Examiner* — Stephen Akridge
(74) *Attorney, Agent, or Firm* — Duane C. Basch; Basch & Nickerson LLP

(57) ABSTRACT

A method and apparatus for dispensing objects from automated storage and retrieval systems such as medications is disclosed which may also include a singulator to assure singulation (retrieval of singular objects). The singulator may be an imaging system to confirm and/or identify the objects being dispensed and/or a variable orifice dynamically adjustable to a specific object or pill size, and through which only a single object or pill is allowed to pass. The system may further include a flexible probe so as to reduce the size of the system where the movement of the probe relative to or while retrieving objects is accomplished by advancing/retracting a flexible tube. The method and apparatus may further include an imaging system.

19 Claims, 28 Drawing Sheets

(56) References Cited

U.S. PATENT DOCUMENTS

| | | | |
|---|---|---|---|
| 5,790,409 A | 8/1998 | Fedor et al. | |
| 6,732,884 B2 * | 5/2004 | Topliffe | A61J 7/0481 221/10 |
| 7,875,245 B2 * | 1/2011 | Favuzzi | B01L 3/508 422/403 |
| 8,020,724 B2 * | 9/2011 | Remis | B65B 5/103 111/179 |
| 8,060,246 B2 | 11/2011 | Berg | |
| 2003/0024943 A1 | 2/2003 | MacDonald | |
| 2008/0020467 A1 * | 1/2008 | Barnes | G01N 35/0092 436/2 |
| 2008/0061074 A1 | 3/2008 | Remis et al. | |
| 2009/0112360 A1 * | 4/2009 | Berg | G07F 9/026 700/231 |

OTHER PUBLICATIONS

EP13823498.4 Unofficial Extended European Search Report with Supplementary Search Report and Search Opinion dated Jul. 11, 2016, corresponds to U.S. Appl. No. 13/948,385; Inventor Michel J. Berg et al.

* cited by examiner

OBJECT DISPENSER HAVING A VARIABLE ORIFICE AND IMAGE IDENTIFICATION

This application claims the benefit of priority from U.S. Provisional Application 61/674,561 for an "OBJECT DISPENSER HAVING A VARIABLE ORIFICE AND IMAGE IDENTIFICATION," filed Jul. 23, 2012 by Michael J. Berg et al., which is hereby incorporated by reference in its entirety.

The disclosed systems and methods are directed to an automated dispensing apparatus that reliably retrieves an object from a group of randomly ordered objects held within containers. In addition the system may include an apparatus and method to singulate and even identify the objects. More particularly, one embodiment is directed to an automatic medication dispensing apparatus for use by patients, which provides for the selection, retrieval, identification and dispensing of a plurality of pills or similar objects, along with logging and tracking of the pills dispensed. Various disclosed embodiments and features add to the robustness and verifiability of the dispensing system.

BACKGROUND AND SUMMARY

In many materials-handling applications, automated storage and retrieval systems are utilized to store and retrieve objects. Some systems are designed to retrieve singular objects from bins containing a multiplicity of objects, such as a system supporting an automated assembly line, wherein the storage and retrieval system might have a plurality of bins, each bin containing a multiplicity of a particular size of fastener.

Medications in the form of solid pharmaceuticals such as pills, capsules, tablets, and the like are traditionally provided in the form of a disposable plastic container having the medication name, dosage and provider printed on the label. The term medicament is used herein to refer to a solid medication in the form of a pill, for example, a tablet and a capsule. Patients taking a plurality of prescription medications, frequently exhibit poor compliance in properly following a particular drug regimen. It is typical for the medications to be taken in varying dosages, on various days, and times. Geriatric patients, particularly those having impaired eyesight, mental acuity and other cognitive, motor, or sensory dysfunctions are a leading group who make medication mistakes resulting in missed medications, errors in intervals or improper dosages. Even people with intact function often have difficulty maintaining medication regimen adherence, especially when they are prescribed multiple chronic medications. A variety of products and techniques for reminding patients of their medication regimens are known, however, to date have had limited success as a result of cost, reliability, complexity, inadequate utility and lack of "fail-safe" operation.

In the various embodiments described herein, it is important that the retrieval system retrieve and deliver a precise quantity of the desired objects or objects. Frequently the desired quantity of objects is one. Quantity precision for quantities larger than one object can be obtained by multiple retrievals of singular objects.

Additionally, in the embodiments described herein, a user friendly design is important. Using a vacuum probe for the pick and place system can improve the design, for example by permitting the use of the vacuum pressure as an indication of the successful pick or retrieval of an object or item such as solid medicaments. The use of a carousel design, with a plurality of bins or containers placed in a side-by-side relationship around the carousel permits the storage, and retrieval, of a plurality of object types or medicaments, and makes the disclosed embodiments appropriate for dispensing medication for personal use. Furthermore, the use of open-top containers, as disclosed in embodiments herein, significantly improves the ease of loading, reloading and refilling the containers with items such as pills, and also allows the retrieval probe to be moved laterally within the container to interrupt bridging and to "search" for items to be retrieved from the container.

In the various embodiments described herein, it is also important that the correct object is retrieved. Identification of the object and confirmation that the object is correct is particularly of concern if the bulk compartment could be loaded improperly. Thus, confirmation that the bulk compartment was loaded with the correct objects or confirmation that the correct object is retrieved is a possible feature of the disclosed embodiment. Identification of the object can be performed by acquiring at least one picture or digital image of the object and using image recognition computer algorithms that extract various characteristics of the object and compare those to a reference database containing identifying information about the objects. The image may also be stored or logged as a record of the medicament that is retrieved and dispensed.

In the health care industry, automated and manual dispensing devices have been used to segregate, and control the dispensing of a wide range of medicaments, such as pills, vials, and packets, to ensure that the prescribed dosage is administered at the intended time interval. An example of a dispensing system is disclosed, for example, in U.S. Pat. No. 7,502,664 (issued Mar. 10, 2009) and U.S. Pat. No. 7,587,259 (issued Sep. 8, 2009) both by M. Berg; the entire contents of said patents being hereby incorporated by reference for their teachings.

Additionally, refills, expiration and pill inventory are supplemental features of an automated dispensing system. Generally speaking assisted pill dispensing of a prescribed dosage of a plurality of pills have customarily been manually prepared in partitions within a pill containment tray or case, whereby an associated alarm device or clock advises the patient or care giver that it is time to consume the next compartment of medications. Alternatively, a pharmacy may package a prescription in a "blister pack" or other specialized packaging, which is engaged into a dispensing mechanism that retrieves each pill on a pre-programmed basis. Programmable dispensing devices for in-home use are also known.

Presently, there exists a need for a system that provides an effective solution for both patients and health care providers regarding the patient's adherence to medication and dosage regimens. Such a system should enhance the interaction between the patient and health care provider by reliably dispensing medications for patient use, while allowing the health care provider to monitor the medication intake and program the medication regimen. Such a system should also provide a "recovery" or restocking process, including the ability to recycle medications that were not taken on time, so that medications are not wasted when a patient fails to retrieve medication.

A common method for retrieving small objects from storage bins is to utilize a vacuum probe with tip, associated with a retrieval mechanism. When the probe is connected to a vacuum pump, or other vacuum source, an inrush of air occurs creating a pressure differential that in turn acts on objects in proximity to the probe tip. The pressure differential urges the objects toward the probe tip until the object obstructs the opening of the probe tip, creating a vacuum force that holds the object onto the tip, which in turn allows the retrieval mechanism to lift the object. The vacuum probe can be said to have gripped or grasped the object by the application of the vacuum pressure.

Although primarily discussed herein as a system and method designed to "grip" and retrieve solid pharmaceuticals, it will be appreciated that aspects of the disclosed embodiments may employ alternative gripping or retrieval mechanisms. For example, when a storage bin holds magnetic objects (e.g., ferrous objects such as steel screws), the retrieval mechanism may employ a magnetic tip. With such retrieval methods, it is also conceivable that the retrieval mechanism may, in fact, lift more than a single object from the bin or container in which it is stored. To prevent or reduce the probability of a multi-object retrieval in accordance with the disclosed embodiments, an apparatus suitable for singulating objects, or a "singulator," may be employed to assure that only a single object is removed or dispensed at a time.

One example of a singulator that may be employed with embodiments disclosed herein is an aperture through which the object must be retrieved, where the aperture is variably or dynamically sized to permit only a single object to be retrieved—thereby only allowing a single object through the aperture. As will be appreciated based upon the detailed description below, the retrieval probe and tip must be made small enough to pass through the aperture while retaining the at least one object or object. For objects smaller than the probe and tip, the aperture may be adjusted to allow the probe and tip to pass through the aperture orifice and then the size of the aperture can be decreased to permit only one object to pass through.

When retrieving objects which may have a primary dimension significantly greater than others, such as machine screws, where the length often is much greater than the diameter, or such as pharmaceutical caplets or capsules, where the length may exceed the diameter(s), the required restrictive aperture may often be smaller than the length dimension of the object being retrieved. If the object is attracted to the tip of the retrieval probe (e.g., with the long side of the object making contact with the tip), it would be impossible for the object to be retrieved through an aperture smaller than the long dimension of the object. In practice, it is observed that if the attractive force between the tip and object being retrieved is sufficient, the object may actually reorient itself relative to the retriever probe tip, for example when the restrictive aperture is encountered by the object, as the retrieval mechanism attempts to move the object through the aperture. The reoriented object may, therefore, present a smaller dimension, cross-section or less-restrictive profile/shape to the aperture, and may successfully pass through the aperture. Tapering the surfaces surrounding the aperture opening, for example as a cone-shape tapered in a direction toward the aperture opening, increases the probability that the object will successfully reorient itself.

While a bin top with a fixed aperture reduces the probability of multi-object retrieval for objects of a common size, it requires that the aperture size be matched to the objects to be retrieved therethrough. Such an aperture, however, does not necessarily prevent a second object from following a first object through the aperture. Furthermore, it requires predetermination of the appropriate aperture size for the objects stored in each storage bin. An aperture with a variable orifice with dynamic controls is disclosed herein in association with a method to singulate objects.

Another example of a singulator disclosed herein is a digital image capture apparatus and associated image processing circuitry by which a plurality of images of the retrieved object(s) is analyzed to determine whether a single or multiple objects have been retrieved. An image-based singulation apparatus may further enable the characterization and/or verification of the object type to assure that an appropriate medication (e.g., pill type) has been retrieved for dispensing. Furthermore, the use of a plurality of singulation techniques, in combination, is also contemplated.

For restocking of storage bins fitted with fixed or removable tops the top would have to be removed to allow new content to be added into the bins, and would further require that a correct top be placed back onto that bin. In embodiments disclosed herein the possibility of an error restocking the bins by loading them with an incorrect object is contemplated. Imaging techniques, as noted above, and associated image recognition may also be used to identify such an error before the incorrect object is dispensed.

One embodiment disclosed herein provides a system that includes a dispensing apparatus having a number of storage containers, each of which may contain a different object, an associated temporary or pre-dispense storage container for receiving the different objects retrieved from storage containers, and a delivery tray or cup for receiving and then dispensing the various objects such as solid medicaments. The device further assures singulation of retrieved objects and thereby dispensing of an accurate dosage. An advantage of such a device is that it reliably dispenses the correct dosage level by avoiding an errant pill or the like from passing into the delivery tray or cup. Moreover the dispensing information is recorded or logged and stored in a memory for subsequent use.

Another embodiment disclosed herein provides for reduced overall height of the device with use of a flexible or angled vacuum probe. In one embodiment the flexible vacuum probe can be guided around a radiused angle, such as a ninety degree turn, by: a surrounding fixed sheath forming a channel, a set of pulleys and guides, a set of grooved wheels and guides, or similar components and combinations thereof. Similarly, the disclosed embodiments contemplate the ability to control the position of the vacuum probe relative to a storage container or bin, and thereby facilitate the probe being guided to a specific location in the storage bin to pick up the objects.

As noted above, the use of image-based singulation further provides for the reliable identification of the medication to ensure that the proper medication was retrieved and loaded into the pre-dispense storage compartment and subsequently dispensed to a patient. The system can further store such information to permit the patient, care giver, or other health care provider to verify that the proper medication was loaded.

Operative elements of the disclosed pill dispensing system include a microprocessor, motor(s), a pill retrieval probe, probe tip or proboscis-like element, pill receptacles and an apparatus for the singulation of pills or similar objects being dispensed. More specifically, a retrieval system with a vacuum probe ('pick and place' system) selectively moves a single object or unit of a medicine from one of a plurality of storage receptacles, and then stores the object, along with others, in a temporary storage or pre-dispense container before the used retrieves the collected medications.

Also contemplated in accordance with the disclosed system is a communications interface and protocol, associated with the dispensing apparatus, for on-site and/or remote control of the operation and functionality of the dispensing system. Remote programming can be enabled for the medication regimen which can include adjustments for late or missed doses, and schedules that reduce or increase, over a programmed time period, the number and frequency of objects being dispensed from the apparatus as in a medication titration. Furthermore, a missed dose may be restocked, as needed medications can be programmed with constraints, and allowances can be made to get medication doses early or to get extra doses if a pill or pills are damaged or lost. In addition object (e.g. pill) inventory can be performed by retrieving a programmed number of doses or objects and placing these into the pre-dispense compartment and then restocking the objects once a specified count is reached or the bulk storage compartment is empty (i.e. no further objects can be retrieved from the bulk storage compartment by the vacuum probe and retrieval system). All the information regarding device function including object supply, retrieval, orifice sizes and function, dispensing, restocking, inventory and device errors or malfunctions can be stored within a memory associated with the system and retrieved and/or viewed by appropriate authorized personnel including the health care provider.

Operative elements of the disclosed pill dispensing system also include a pill identification system that incorporates an imaging system or camera(s), light source(s) for appropriate lighting during imaging, possibly mirror(s) for multiple views with a single camera, and an imaging region, area, or compartment, along with a microprocessor with storage for performing the image processing algorithm and accessing a database.

Accordingly, it is an object of the disclosed system and methods to accurately dispense variable medication doses at various times.

Similarly, it is an object of the disclosed system and methods to accurately identify a wide variety of objects including medications with a wide spectrum of shapes, colors, sizes, and markings.

Disclosed in embodiments herein is an object dispensing system, including: a housing comprising a rotatable carousel, the rotatable carousel including a plurality of removable containers where each container provides a repository for objects therein; an access port in the housing through which an object may be removed from each of the plurality of containers, in seriatim; a pre-dispense port in the housing providing controlled access to one of a plurality of output containers (a dispense container and a restocking container); and a retrieval probe, said probe located within the confines of the housing and operatively moving (laterally sliding/swinging) between the access port and the pre-dispense port, said probe including a compliant tip for releasably engaging an object in one of the plurality of containers via said access port, said probe retrieving the object from a container and then moving between the access port and the pre-dispense port to deliver the object to a dispensing receptacle.

Also disclosed in embodiments herein is a medicament dispensing method comprising: providing a dispensing system, including a housing having a rotatable carousel therein with a plurality of removable open-top containers, where the carousel moves under the control of a carousel drive, each container including a repository for objects therein; an access port in the housing through which an object may be removed from the plurality of containers, in seriatim; a pre-dispense port in the housing providing controlled access to one of a plurality of output containers; and a retrieval probe, said probe located within the housing and operatively movable under the control of a horizontal slide drive by a slide motor between the access port and the pre-dispense port, said probe further including a vertical slide retracting and extending the probe and a compliant tip thereon under control of a vertical slide motor, the probe tip releasably engaging an object in one of the plurality of containers via the access port, placing a different medicament into at least two of the plurality of containers; in response to a dispense request, a controller operating to move the carousel to place a container having the requested medicament beneath the access port, and moving the horizontal probe slide into a position so that the probe tip is over the access port, wherein the probe is then extended to engage a medicament, and once engaged by the probe tip, the medicament is raised while attached to the probe tip and retrieved from the container via the access port; said controller then engaging the horizontal slide drive to cause the horizontal probe slide to move into a position over the pre-dispense port; releasing the medicament from the probe tip to deliver the medicament to a pre-dispense receptacle beneath the pre-dispense port; and moving the pre-dispense receptacle, using a pre-dispense slide motor responsive to the controller, to transfer the medicament from the pre-dispense receptacle to a dispense cup accessible by a user In addition, disclosed in embodiments herein is a medicament dispensing system, comprising: a housing comprising a rotatable carousel, the rotatable carousel including a plurality of open-top, removable containers where each container provides a repository for medicaments therein; an access port in the housing through which an object may be removed from each of the plurality of containers, in seriatim; a pre-dispense port in the housing providing controlled access to one of a plurality of output containers; a hollow retrieval probe connected to a controllable vacuum source to provide a vacuum tip at one end that releasably engages the medicament for removal from the container using the vacuum to attach the medicament, wherein said probe retracts upon drawing a vacuum at the tip by contacting at least one medicament and where said probe located within the confines of the housing and operatively moving between the access port and the pre-dispense port, said probe including a compliant tip for releasably engaging an medicament in one of the plurality of containers via said access port, said probe retrieving the medicament from a container and then moving between the access port and the pre-dispense port to deliver the medicament to a dispensing receptacle; a singulator, operatively interposed adjacent the access port, said singulator operating to assure that only a single medicament object is removed at a time by the retrieval probe, wherein the singulator is selected from the group consisting of an imaging capturing device; an iris-type variable orifice, and a variable orifice formed between a pair of rollers each having a cam-shaped recess thereon; a first movable cover associated with both the access port and pre-dispense port; a second movable cover associated with each of the plurality of containers supported by the carousel, wherein the first and second movable covers are operatively engaged to seal the containers and access port and prevent an medicament from being removed from the container when the system is not in operation, wherein the first and second movable covers are operatively connected via a single mechanism employed to coincidently control the engagement and disengagement of both the first and second covers; a processor enclosed within the housing, said processor controlling the operation of the carousel and the retrieval probe to assure that a medicament in a selected container is retrieved and dispensed by the system; a re-stock receptacle to receive any non-dispensed items, said restock receptacle storing the items until a manual intervention results in the items being restocked in an appropriate bin; and a database, stored in memory, for tracking those items that are placed into the restock bin and decrementing the items from a supply of available items, also reflected in the database, until such time as the items are restocked into a respective container.

Figure 1:
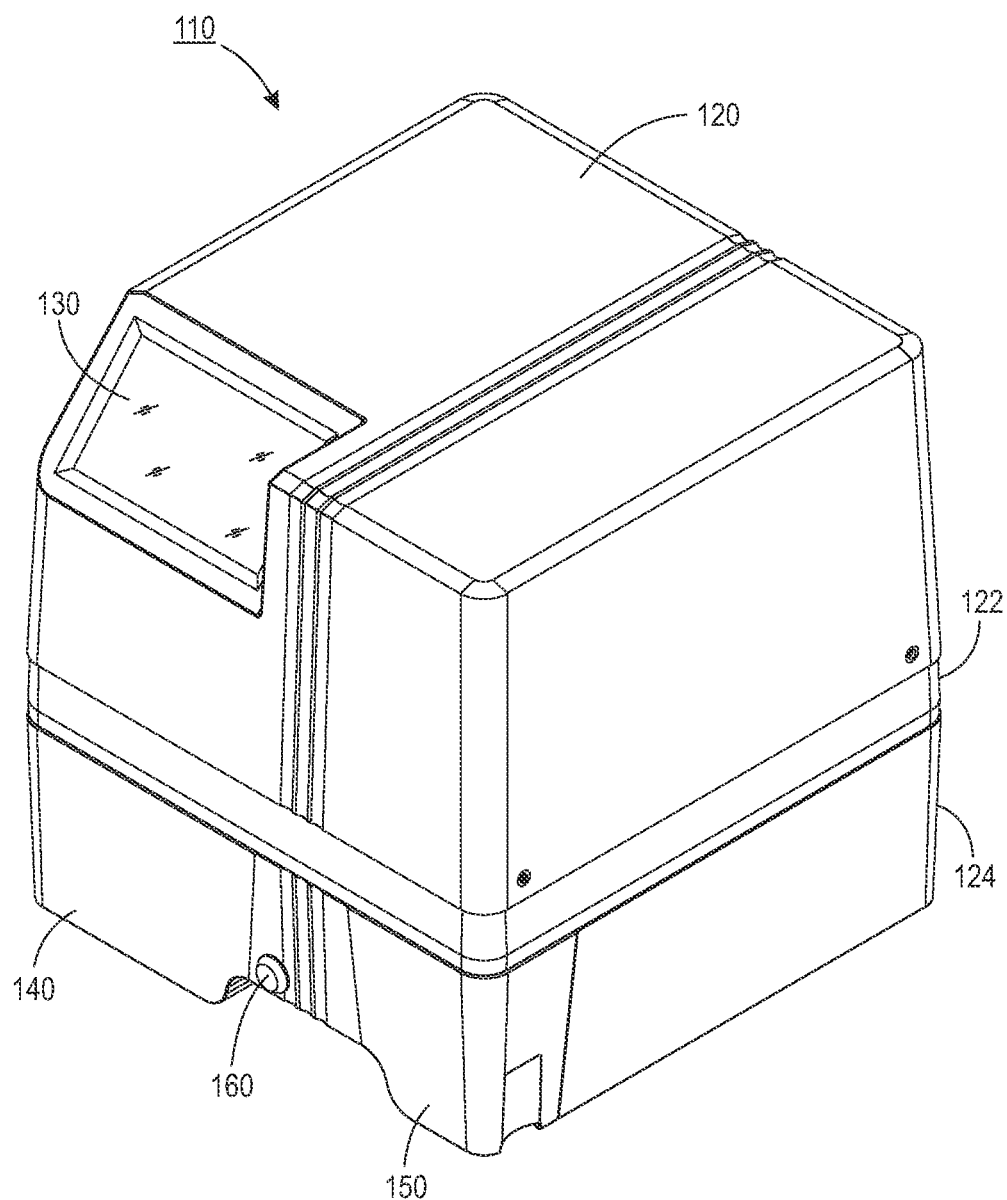
FIG. 1 is perspective view from the front right of a pill dispensing system.

The various embodiments described herein are not intended to limit the disclosure to those embodiments described. On the contrary, the intent is to cover all alternatives, modifications, and equivalents as may be included within the spirit and scope of the various embodiments and equivalents thereof.

DETAILED DESCRIPTION

For a general understanding, reference is made to the drawings. In the drawings, like references have been used throughout to designate identical or similar elements. It is also noted that the drawings may not have been drawn to scale and that certain regions may have been purposely drawn disproportionately so that the features and concepts could be properly illustrated.

Turning first to FIG. 1, shown therein is a perspective view of the front right of a pill dispensing system 110. The system is enclosed by a housing having a top shell 120, a middle support frame 122 and a base 124. The upper shell includes a user interface 130 that includes a touch-sensitive screen enabling the display and selection of menu items. Also referring to FIG. 2, lock 160 is located proximate to restock container 140, and serves to control access not only to container 140, but to the interior of the system as described below.

The system 110 is under the programmatic control of a microcontroller (μC) or similar device suitable for carrying out programmatic instructions that are pre-programmed, as well as sensing and responding to input from the user interface 130. One aspect of the disclosed system is that each of operations of the system, and in particular the pill retrieval and dispense operations, have a direct relationship and entry into a data file or log entry that is saved and stored in a resident or remote memory (e.g., 456 in FIG. 10A) in order to retain specific information relative to the medicament or other objects contained therein and the dispensing specifications. The stored information also includes the name of the medication, the quantity to be dispensed, the frequency and time for dispensing, a count of the total number of pills stocked, dispensed and other relevant pharmacologic information including dosing protocols, surface coatings and possibly instructions on how to take the medication. For example, such information may include information such as regular dosing, titration schedules (tapers and dose escalations), late or missed medication protocols, early or damaged medication dose rules/restrictions for extra medications, adjusted dosing based on physiological parameters, and information about other doses that may contradict subsequent doses as well as medication contradictions, including personal contraindications such as allergies. Another use of the stored information could be in the event of a malfunction or damage to the dispensing system. In such a case, it may be possible to export or synchronize the data stored in one machine with a replacement system, thereby reducing the number of steps required for a caregiver to set up the replacement system. Also contemplated is the ability to communicate information, where the system may include its own wired or wireless communication capability (e.g., transceiver, cellular or digital communication device, etc.), where the system may be configured to send a notification such as a voice or text message to a caregiver upon determining a missed dose or event.

Additionally, the form factor, color, markings, and size of the pill may be recorded, the purpose for which will become apparent in the following disclosure. The stored information can include instructions and messages if the medication is a pro re nata (PRN); such as with a "take as needed" medication for pain, in which case the time between doses, the maximum number of PRN medication that can be taken per time interval, the number of pills in the dispenser, the last time the medication was taken, the acceptable timing between medications, the rules for PRN medications (i.e., maximum dose and minimum time interval between doses) all may be set and monitored. All dispenser information and actions can be stored in memory for local or remote access by authorized personnel.

Figure 4:
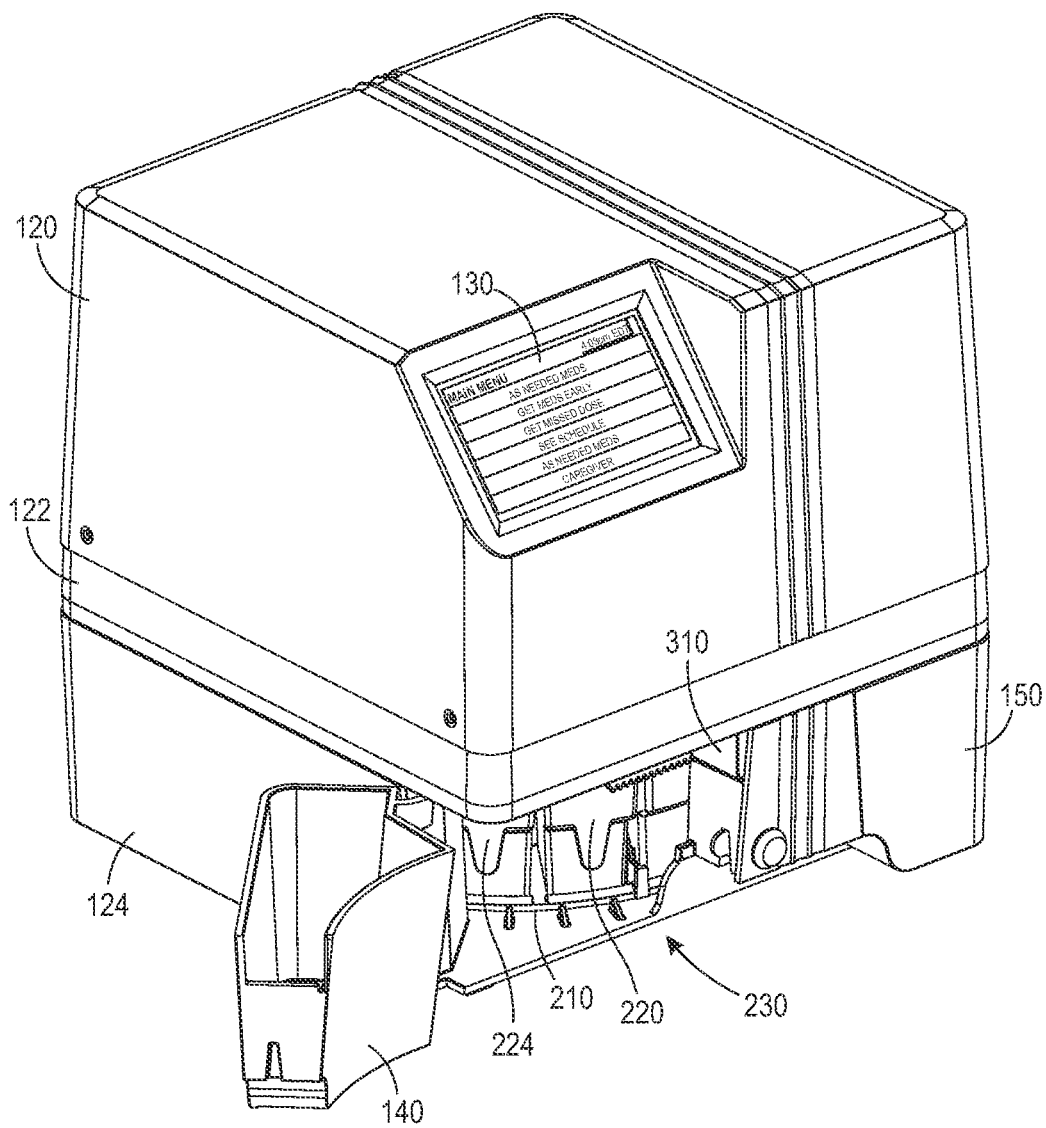
FIG. 4 is a perspective view from the front left of the pill dispensing system showing the restock drawer in an opened position.

Use of the system generally falls within one or a group of operations, including loading/programming the system, pre-dispense operation of the system in a scheduled or as-needed dispense mode, and the actual dispense of medicaments to the user. While these groups of operations will be described further below, the various external features of the system that facilitate such operations will now be described. For example, restock container 140, as depicted in FIG. 4, swings open once unlocked, to permit access to the contents of the container itself. Referring briefly to FIG. 4, with the restock container in the open position illustrated, a user is able to see and access the rotatable carousel 210 and individual bins (e.g., 220 and 224) therein.

As used herein the terms bins and containers are used to describe a receptacle or similar component suitable for holding a plurality of objects therein such as medicaments that have been or will be retrieved. In the disclosed embodiments, the "pie-shaped" bins are arranged on the rotating carousel; however, alternative arrangements such as rectangular bins in an x-y Cartesian coordinate system are possible. It will be appreciated that the bins 220 and 224 are of different sizes, and the design of the system is such that a plurality of bins are spaced around the periphery of the carousel. The bins are also designed with sloped or angled inner surfaces on the bottoms of the bins to encourage medicaments to collect or move into a central portion of the bin for retrieval. As illustrated, for example in FIG. 11A, the bins have at least a sloped outer surface 226 and a sloped inner surface 228, and sloped side surfaces are also contemplated. However, the bins each employ an open-top design so that in the event it is necessary to search, or "dither," by moving retrieval probe position relative to the bin, it is possible to cover the full extent of the bin bottom surfaces.

The system is also designed to allow one to program the system to employ various sizes of bins for particular uses. For example, larger bins may be used for larger medicament sizes and/or for medicaments that are dispensed in greater quantities, whereas smaller bins may be used for smaller or more infrequent medicaments. Bins 220 and 224 are removable and are generally open-top, wedge-shaped containers that sit on the carousel. They are held in relative position not only by adjacent bins, but also by a magnet or other retention mechanism placed on the bin or carousel itself. The bins 220 and 224 are retained on the carousel 210, and when time for filling, replenishing or restocking, the bins are index into the access region 230, adjacent the rear of the restock container. Depending upon the need, other bins may be successively indexed into this area for filling, refilling, restocking, etc.

FIG. 4 also illustrates a pre-dispense receptacle 310 and an associated toothed slide 316 in the top portion of the access region 230. Operation of pre-dispense receptacle 310 will be described in more detail relative to the operation of the system, but it serves the purpose of collecting objects such as medicaments and holding them until either the user initiates dispensing through dispense cup 150, or they are moved to the restock container 140 (e.g., when the user fails to retrieve them within a prescribed time period, resulting in a missed dose).

Figure 2:
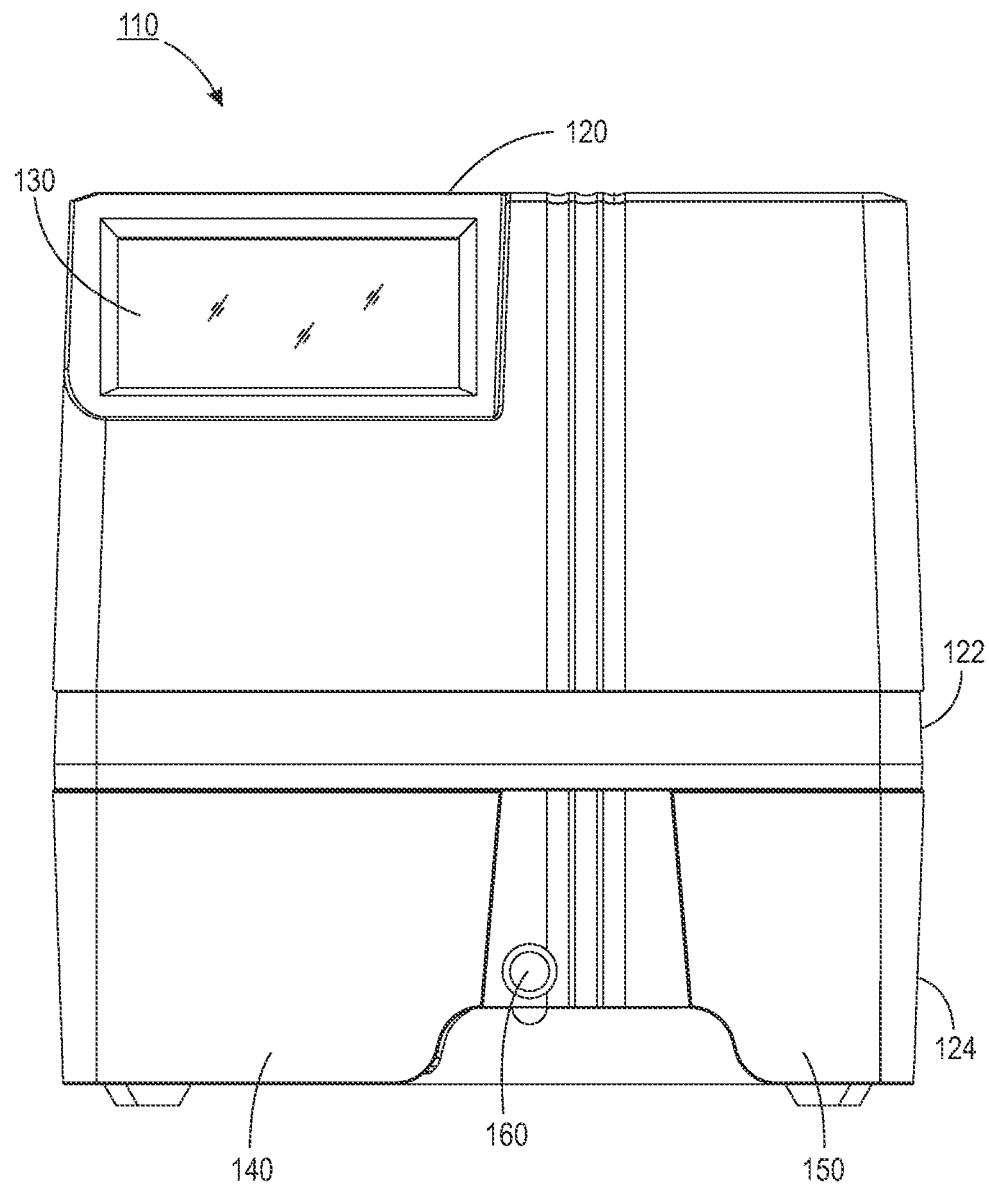
FIG. 2 is front view of the pill dispensing system of FIG. 1.
Figure 3:
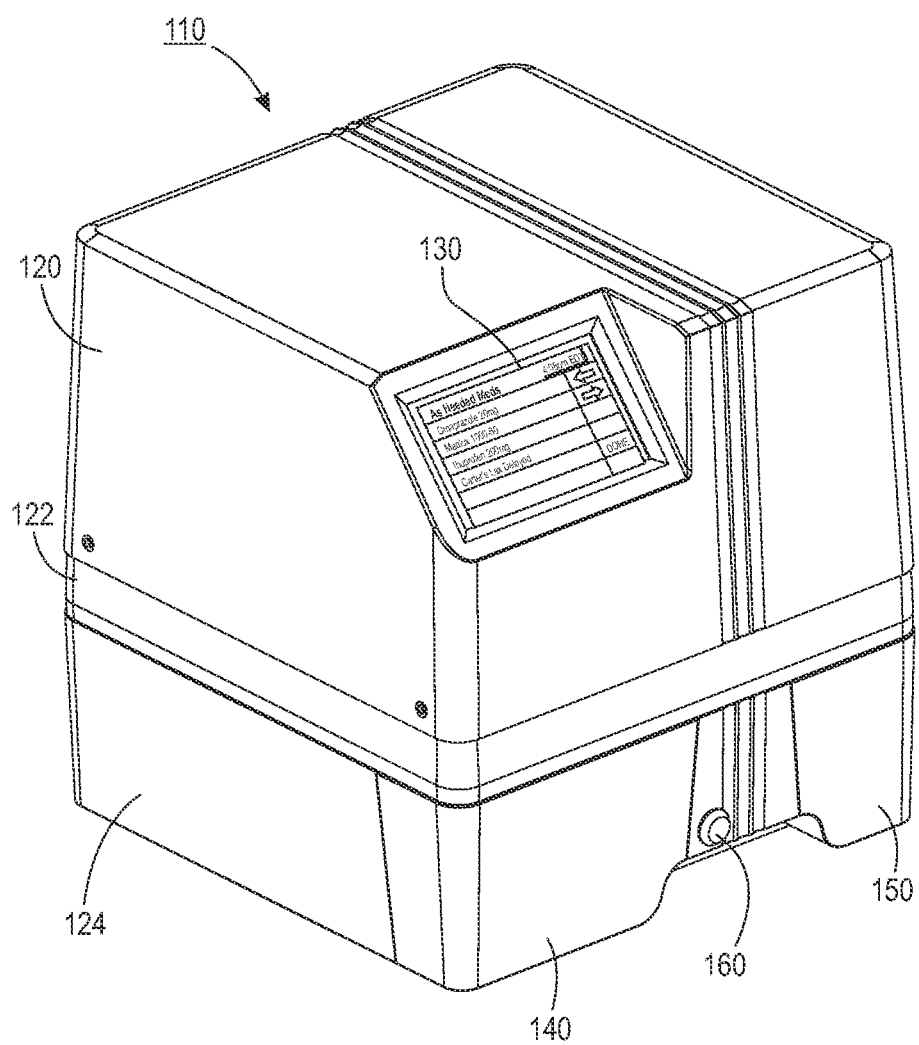
FIG. 3 is a perspective view from the front left of the pill dispensing system of FIG. 1.
Figure 5:
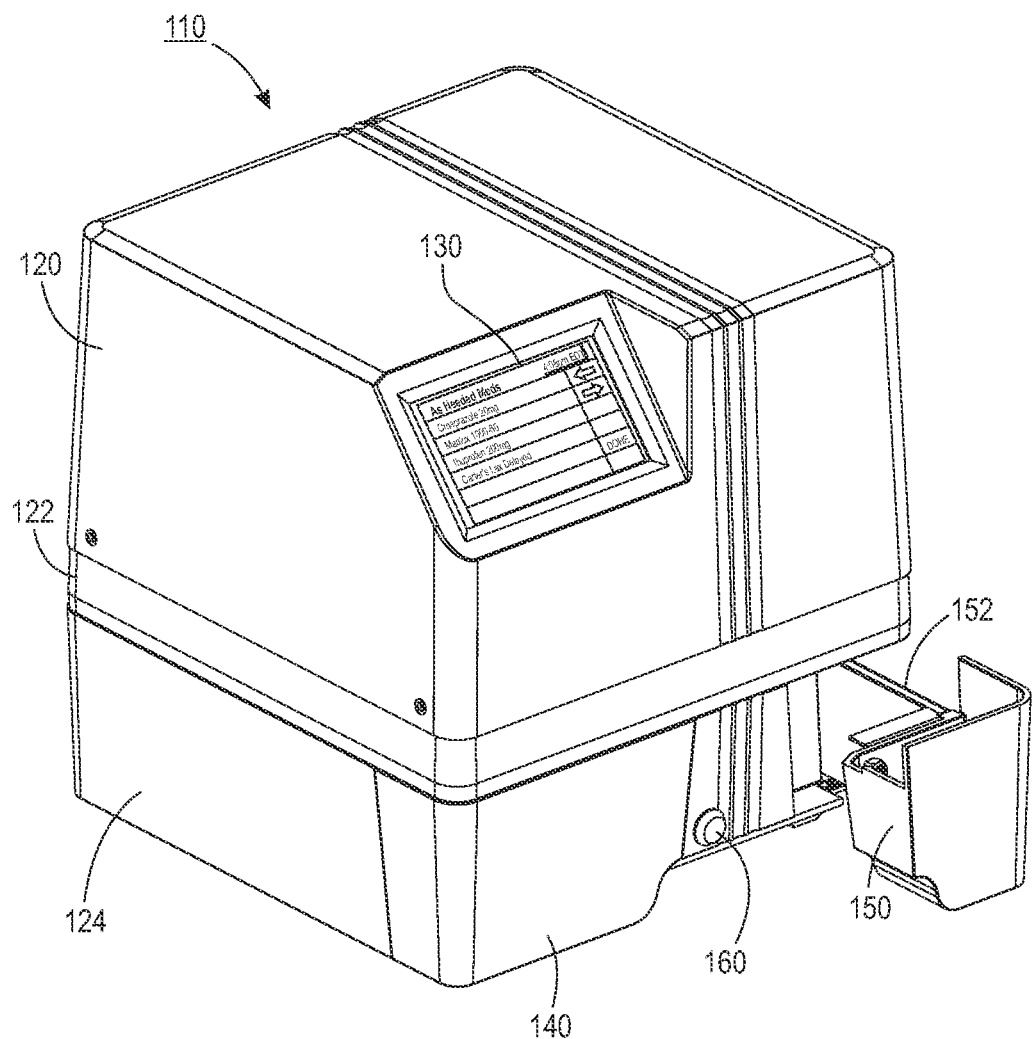
FIG. 5 is a perspective view from the front left of the pill dispensing system showing the dispense cup in an opened position.
Figure 6:
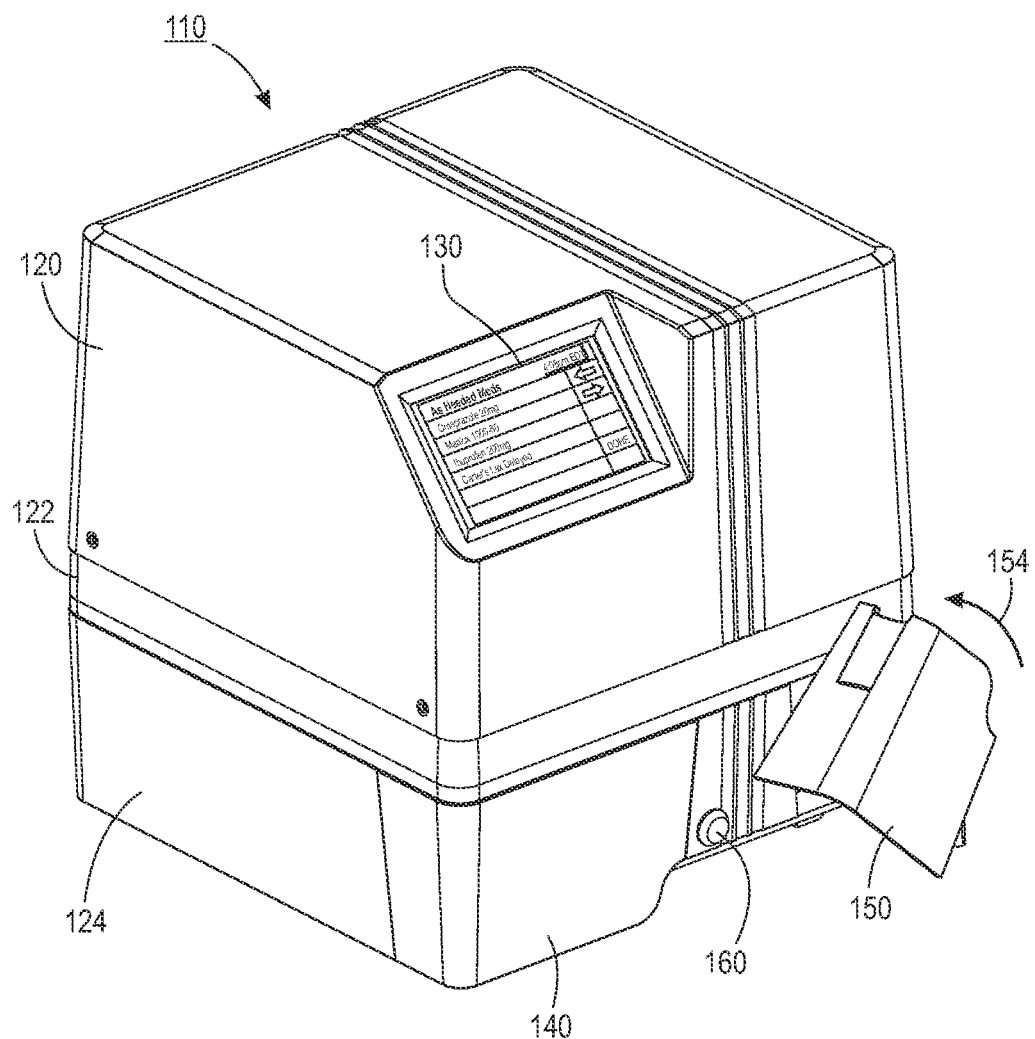
FIG. 6 is a perspective view from the front left of the pill dispensing system showing the dispense cup in a rotated position.

Also referring to FIGS. 2 and 3, depicted therein is a dispense cup 150 that is movable between a first or closed position as depicted in FIGS. 1-4 and a second or open position as depicted in FIG. 5. Movement of the dispense cup 150 between the first and second positions is via a slide, a component 152 of which is illustrated in FIG. 5. Referring also to FIGS. 5 and 6, the dispense cup 150 is depicted in FIG. 6 in a rotated or "dump" position, where it has been rotated in the direction of arrow 154. The purpose of the rotational feature of the dispense cup is to assure that the cup remains connected to the system, yet provides a way for a user to more easily access small items such as medicaments located in the bottom of the cup. Moreover, a user may place his/her hand below the dump position in order to have the dispensed objects (e.g., pills) fall into the user's hand. The use of a dumping cup is believed to be advantageous as compared to other dispense receptacles (e.g., dispense slots or trays) because by inverting the cup it assures that all items are removed.

Figure 7:
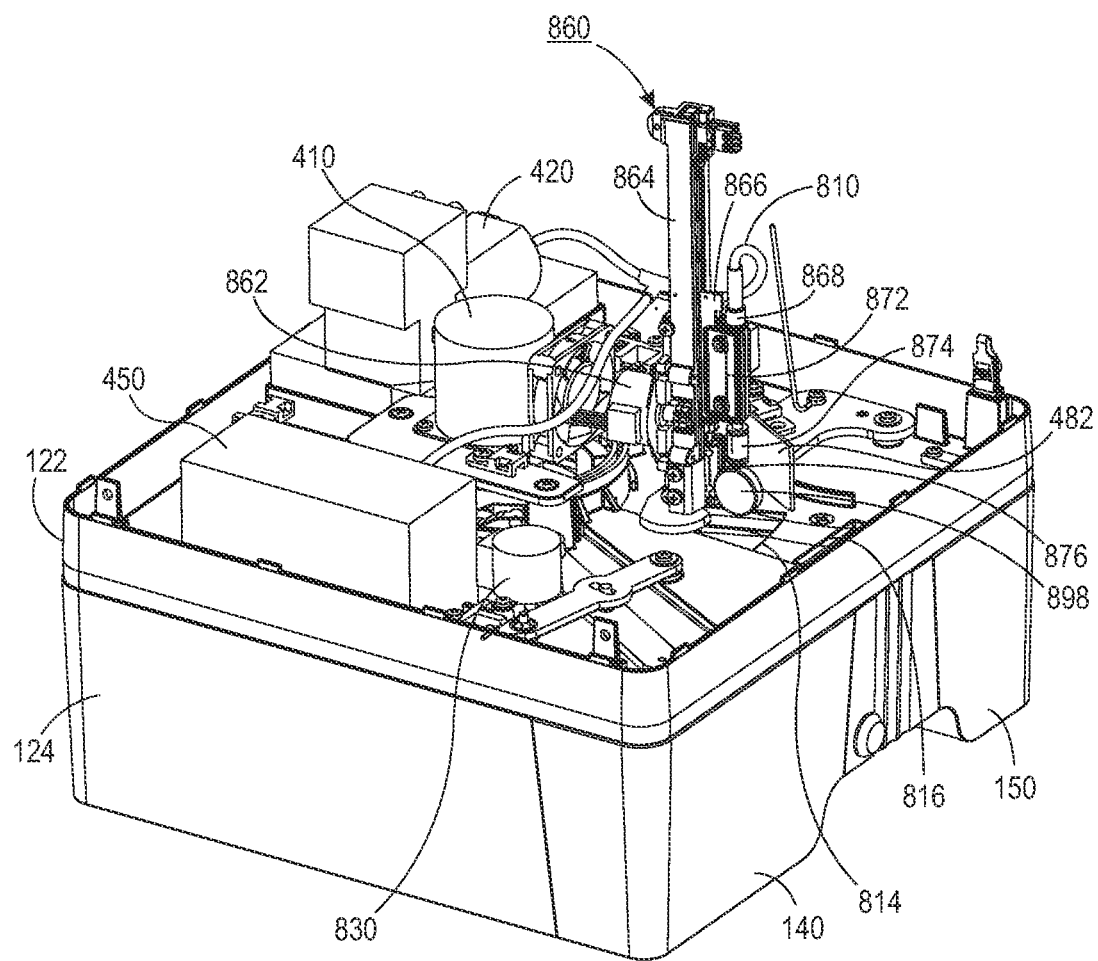
FIGS. 7 and 8 are perspective views of the pill dispensing system with a top cover removed, illustrating the pill retrieval mechanisms in a retrieve and dispense position, respectively.
Figure 8:
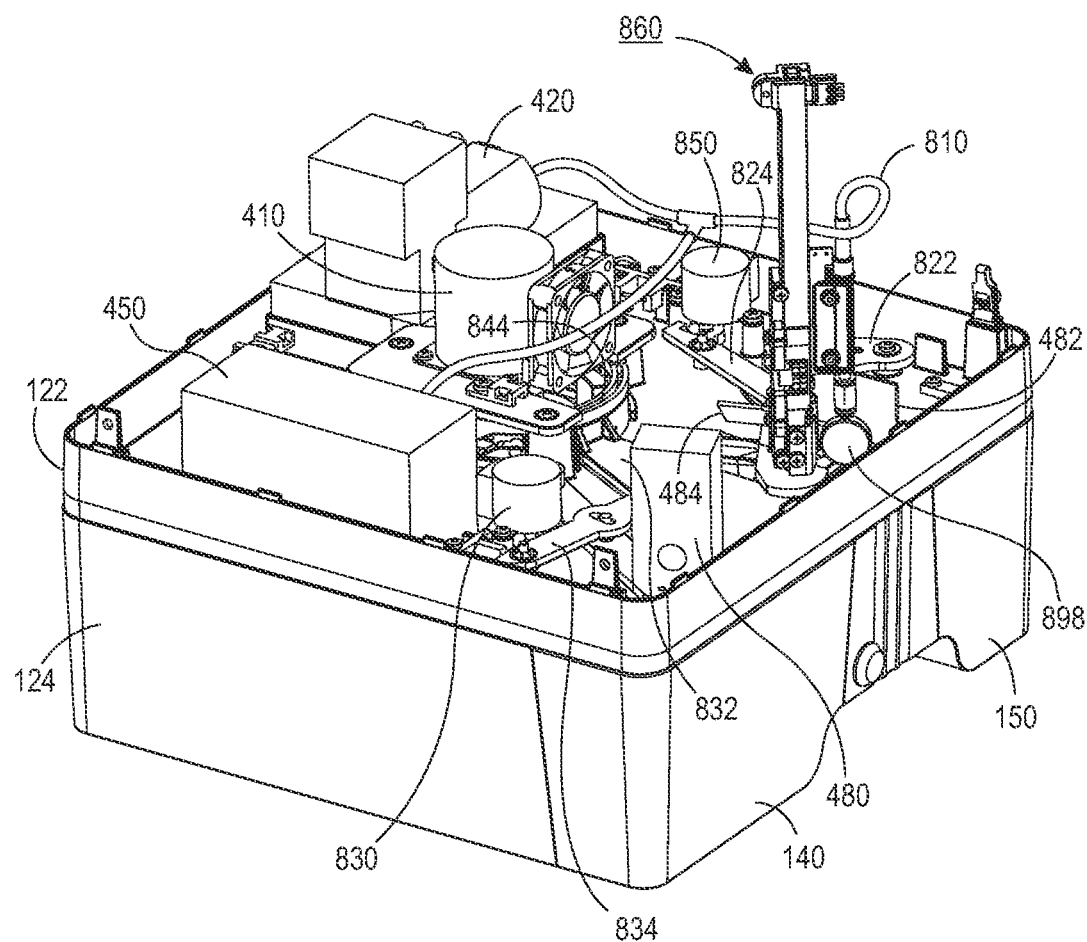
Figure 9:
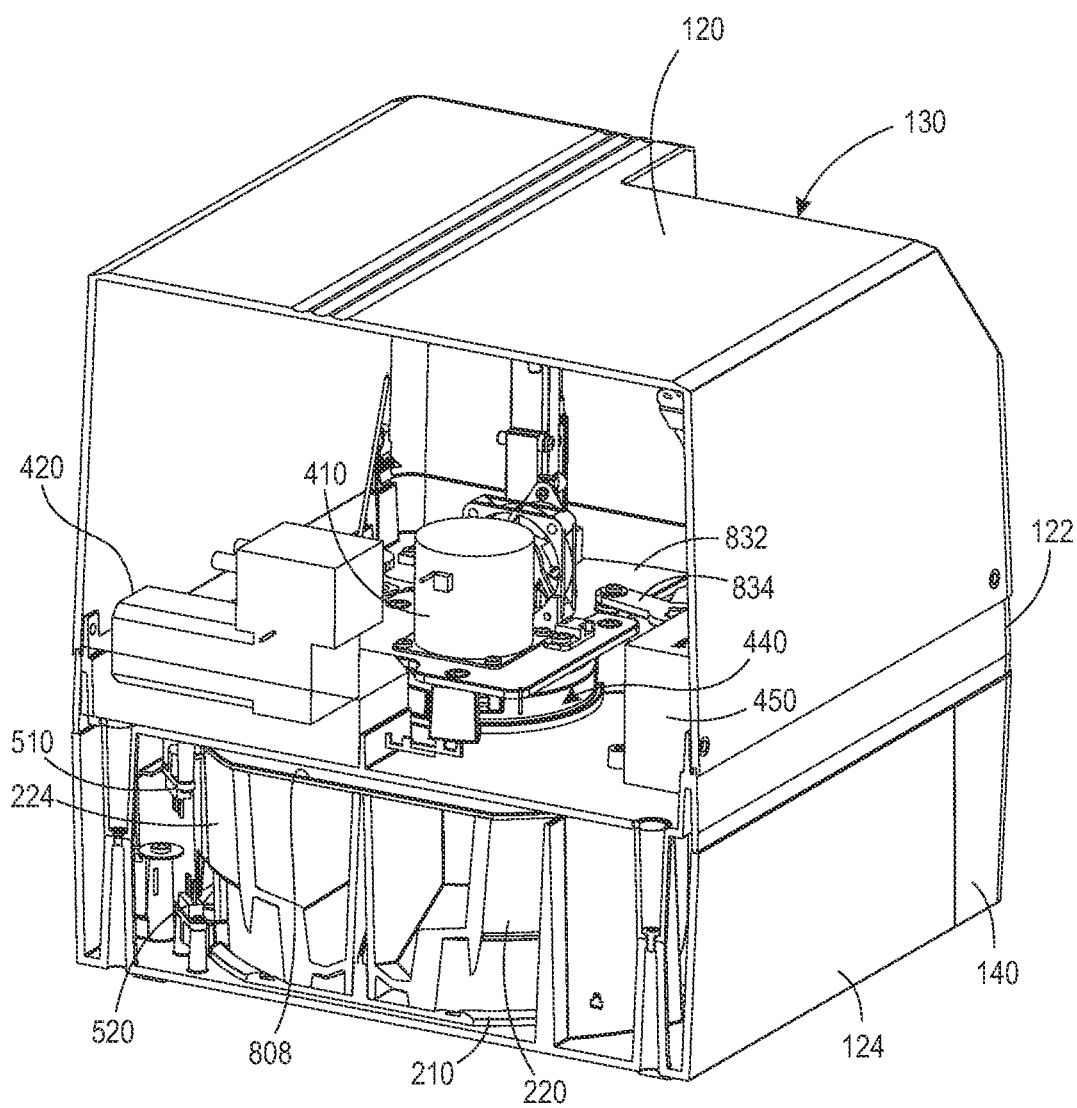
FIG. 9 is a rear perspective cutaway view of the pill dispensing system of FIG. 1.

Having briefly described several aspects and features of dispensing system 110 that are generally visible and accessible to a user, attention is now directed to FIGS. 7-9, showing various views of components within the dispensing system. As will be appreciated, the carousel and medicament bins described above are housed within the lower housing base 124, whereas the mechanisms for retrieving objects from the bins are located on or operatively connected to the middle support frame 122 and enclosed within the top shell 120 (FIG. 9 only). FIG. 7 also illustrates control logic block 450 that includes one or more of the following components that are operatively interconnected to allow the programmatic control of the dispensing system: a microcontroller 454; memory 456; motor drivers 458; and a vacuum sensor 460. The microcontroller is further interconnected with the various sensors and switches described, in order for the microcontroller to be able to sense the relative or actual positions of various components and assemblies in the system.

Figure 12A:
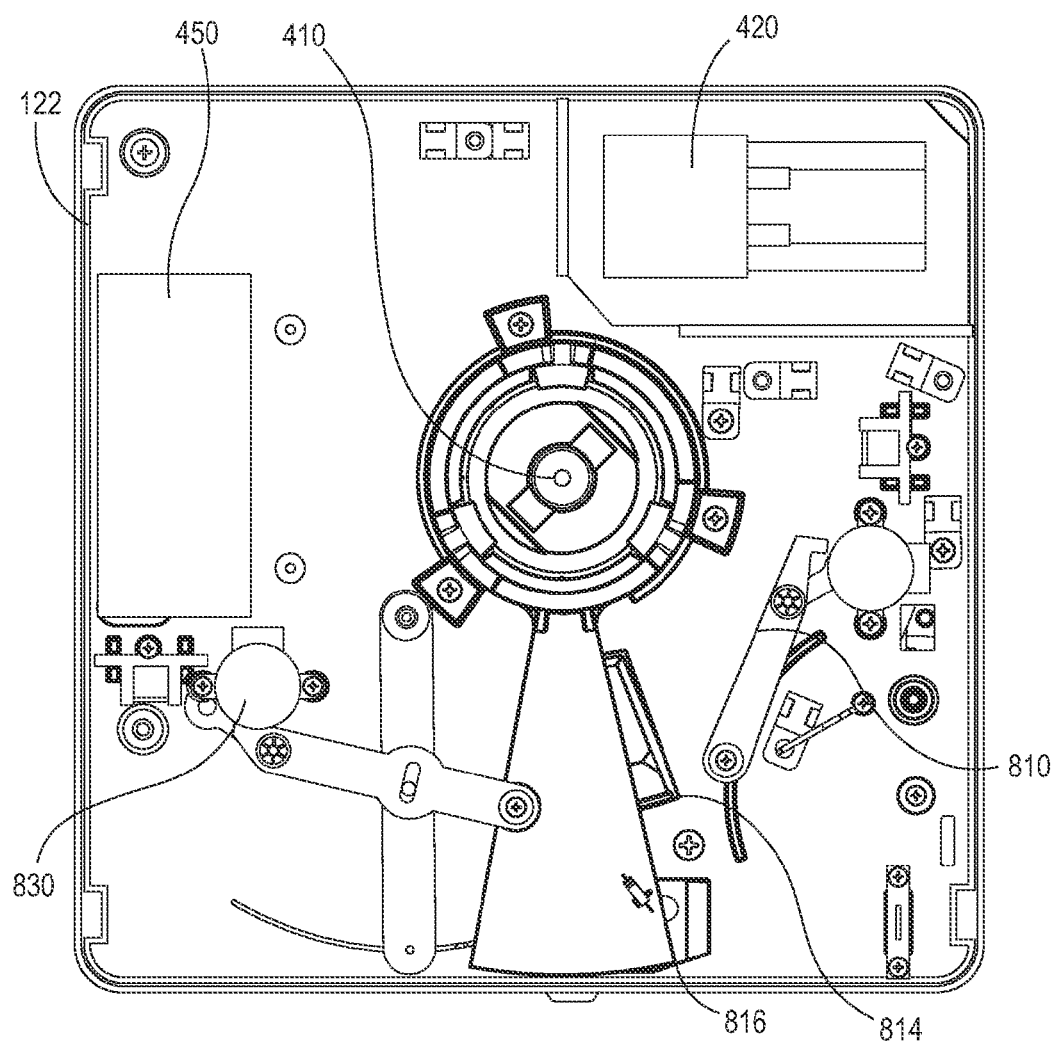
FIGS. 12A and 12B are top views of the cover mechanisms in the pill dispensing system in a partially covered and covered position, respectively.

Once the system has been loaded with medicaments which are assigned to particular bins, and the associated dispensing instructions and schedule have been entered via the user interface and stored in memory 456, the system is ready to operate. When not in use, the system is placed in a "locked" mode, where the open-top bins are covered and access to the medicament bins is prevented except by manually unlocking the restock bin (e.g., key lock 160) and further manual intervention. This assures that any accidental displacement of the system, including movement of the system or travel, etc., will not disrupt the medicaments and cause them to move from one bin to another, or allow medicaments to freely enter the upper portion of the system. A dispense operation of any type, therefore, requires that the system be "unlocked" before any medicament(s) can be retrieved for dispensing. The specific aspects of the unlocking operation will be described relative to FIGS. 12A-12B, below.

Figure 10A:
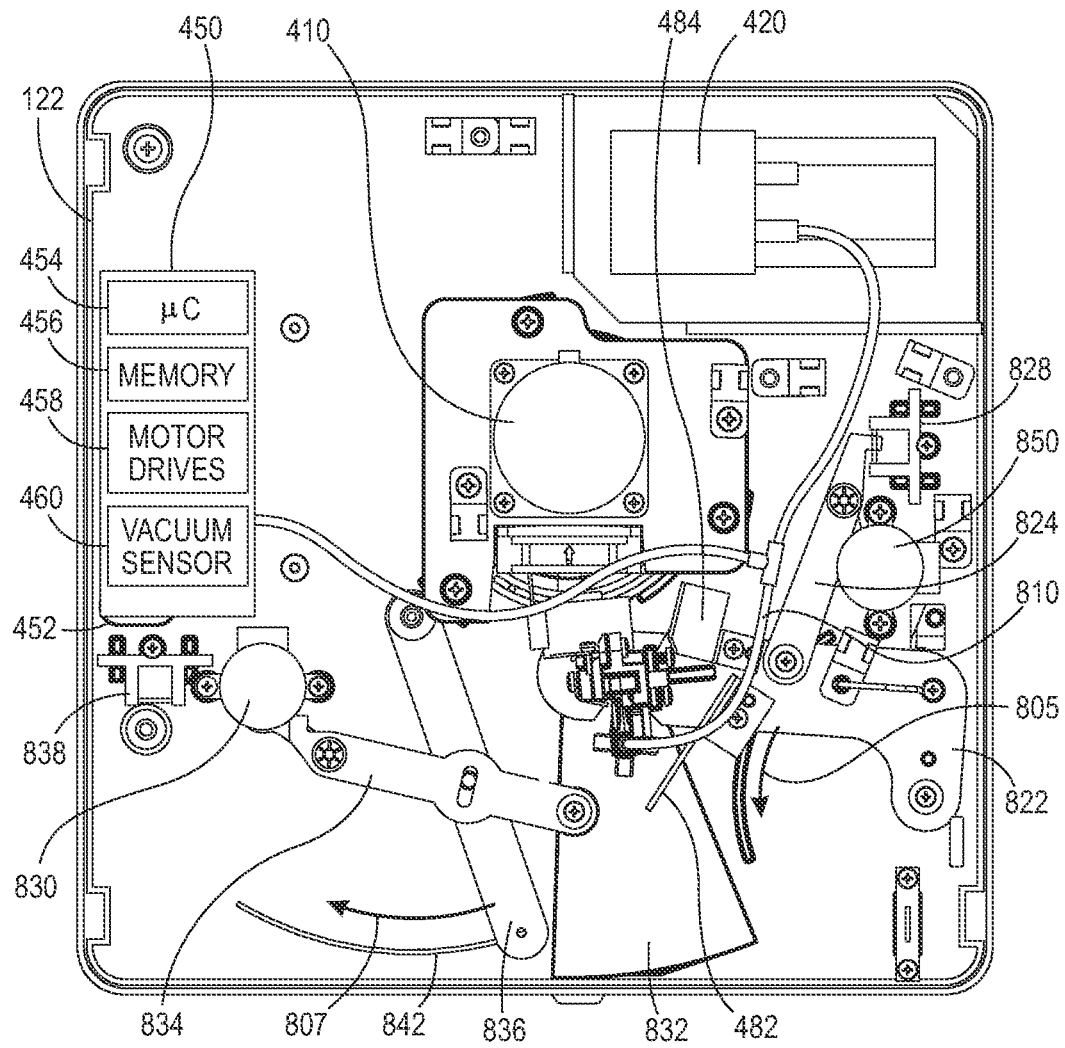
FIGS. 10A-10D are top views of the pill dispensing system with the top cover removed, and illustrating various positions of mechanisms and covers.
Figure 10B:
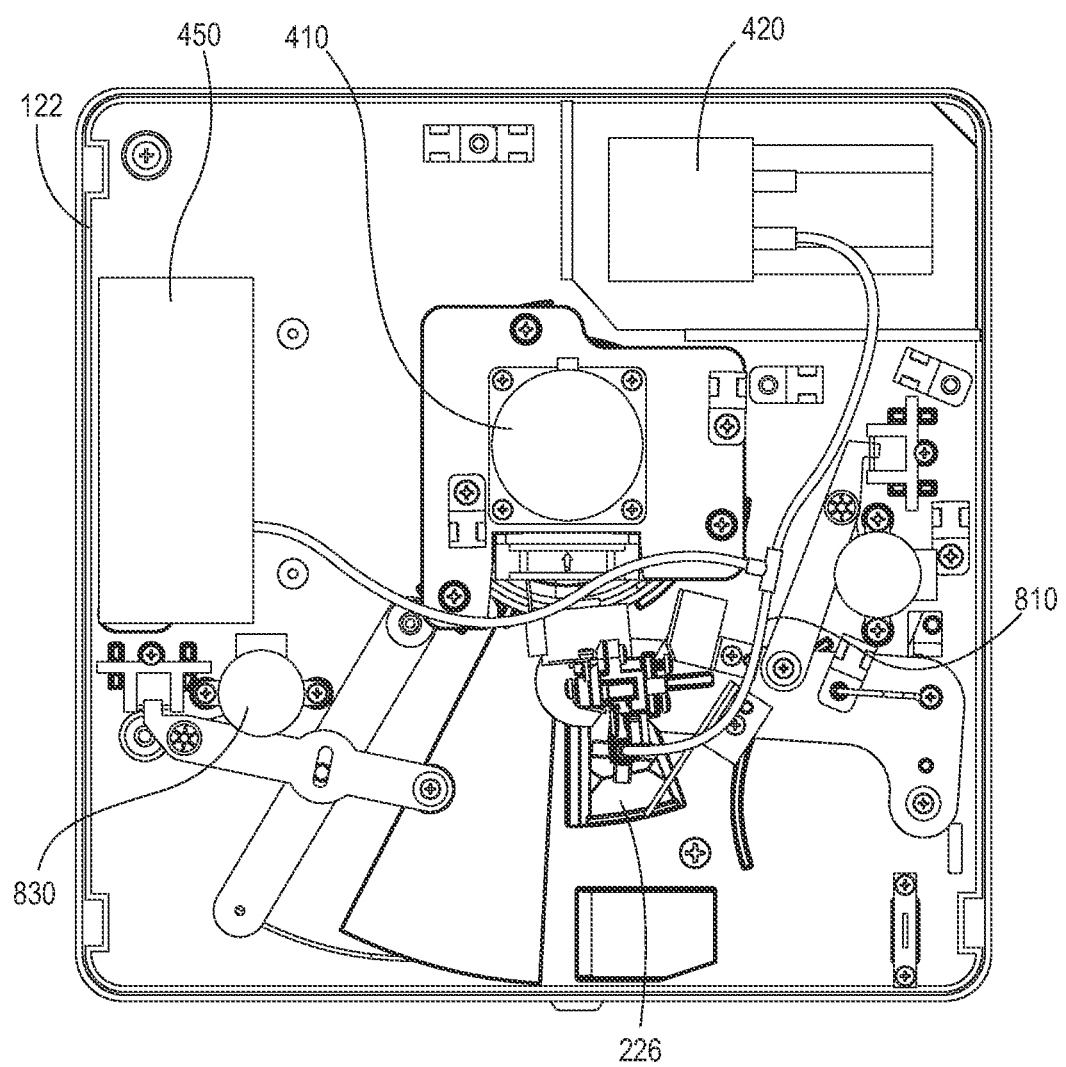
Figure 10C:
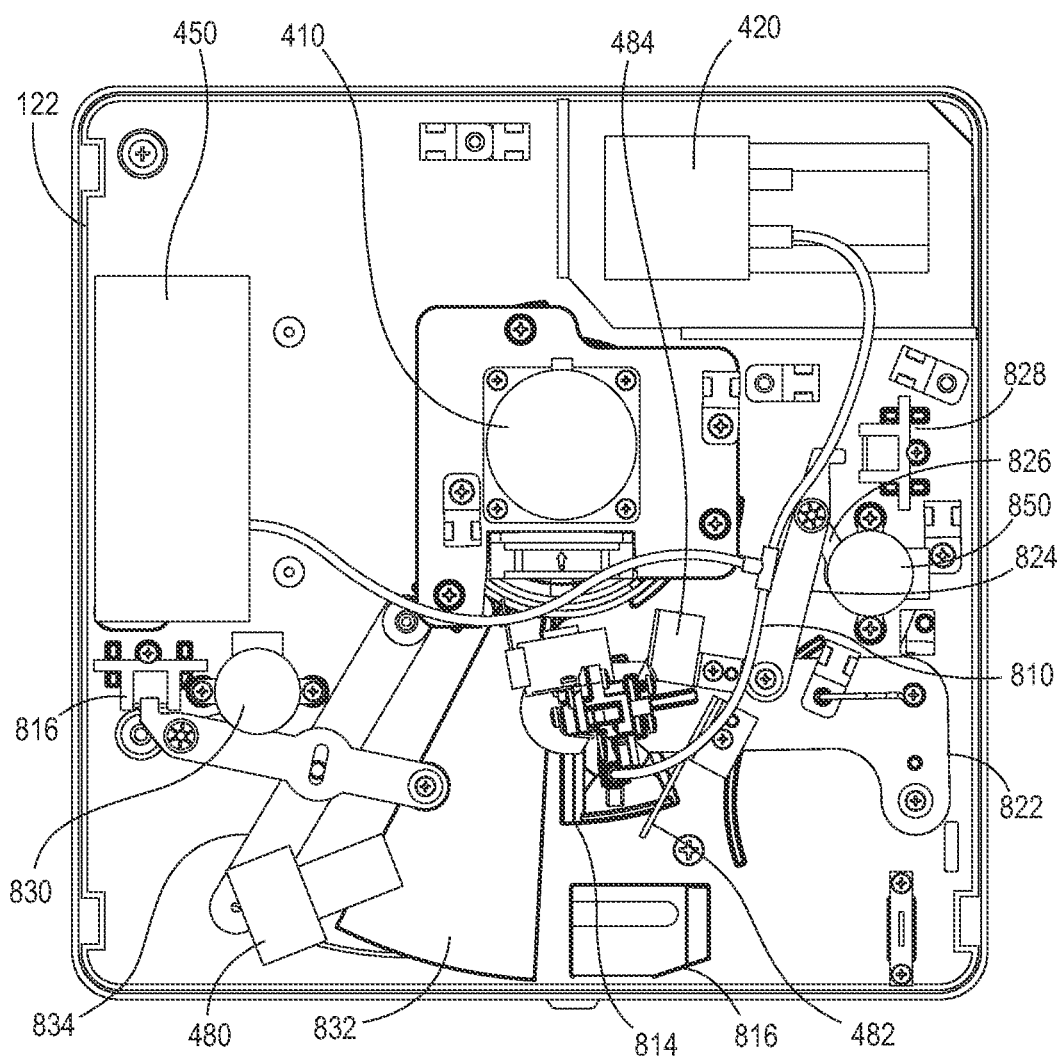
Figure 10D:
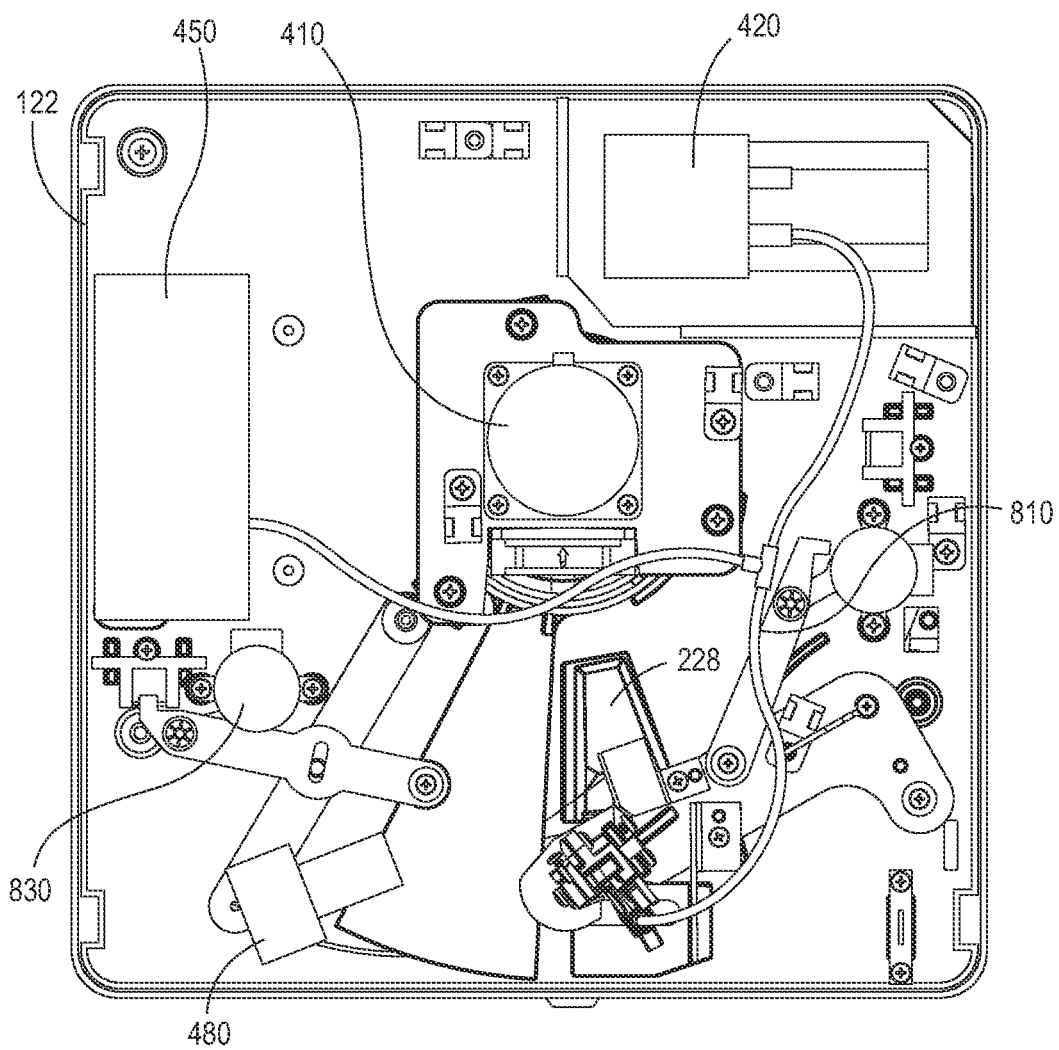
Figure 11A:
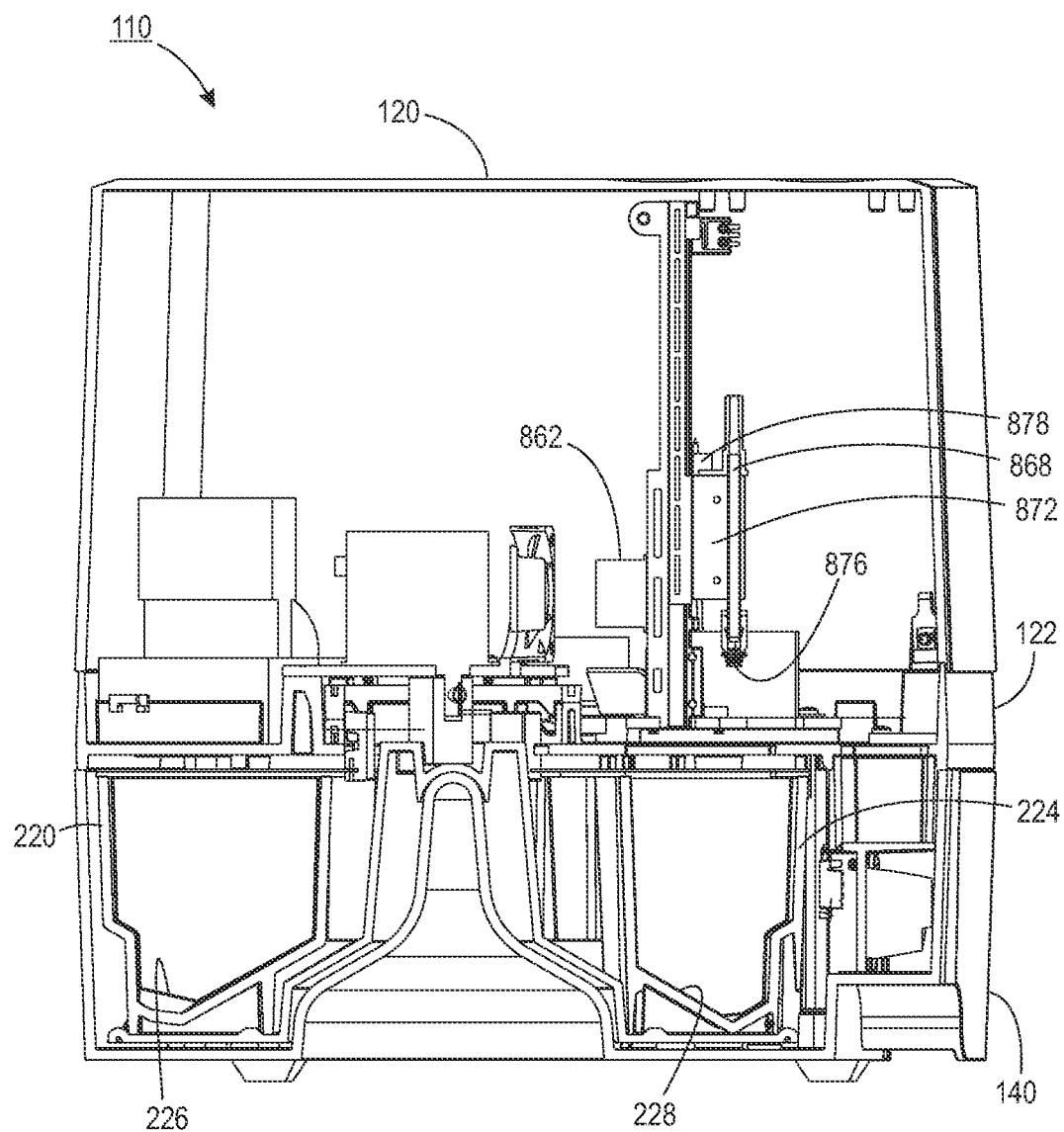
FIGS. 11A and 11B are side cutaway views of the pill dispensing system showing the pill retrieval probe in retracted and extended position, respectively.
Figure 11B:
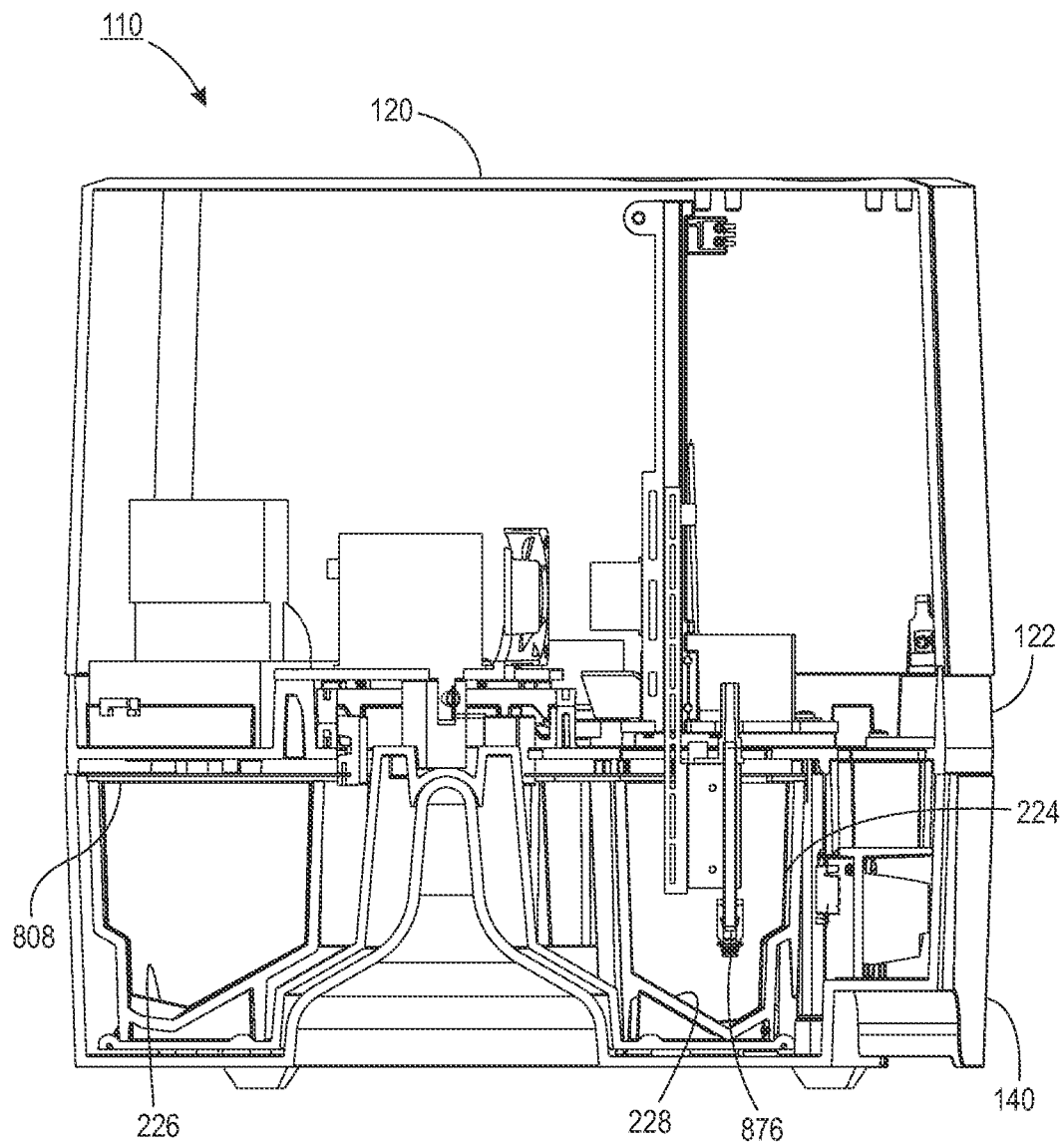

Assuming that the system has been unlocked, prior to a medication being dispensed, carousel 210 is rotated to place a desired medicament bin in a position beneath retrieval probe assembly 860. The side cutaway views of FIGS. 11A and 11B illustrate several positions of the retrieval probe assembly relative to a bin 224. The corresponding horizontal position, above the bin, is depicted in FIG. 7. Referring to FIG. 7, in conjunction with FIGS. 10A-B, the retrieval probe slide motor (e.g., TGM24—Permanent Magnet (PM) Stepper Motors with Spur Gearbox; Anaheim Automation) is used to change the horizontal position of the retrieval probe assembly 860. More specifically, motor 850 is used to move the assembly from the retrieval position depicted in the figures, in the direction of arrow 805 (FIG. 10A), and ultimately to the pre-dispense position as illustrated in FIG. 10D.

The retrieval probe assembly 860 is affixed to the top of retrieval probe slide 822, and the slide is pivotally attached to middle support frame 122 and moved via the retrieval probe slide linkage 824, which is operatively connected to motor 850 via retrieval probe motor linkage 826. The motor 850 may also be a TGM24—Permanent Magnet (PM) Stepper Motor with Spur Gearbox (Anaheim Automation). The retrieval probe position is under the control of motor 850, and is, prior to each operation, "homed" by driving the slide 822 in a clock-wise direction to a home position detected by the retrieval probe home sensor 828. When the free end of retrieval probe slide linkage 824 breaks the beam of home sensor 828, the slide is in the home or retrieve position, and retrieval probe assembly 860 is positioned above the access port 814, which provides an opening to the container below.

When the retrieval probe assembly is in the retrieval position, above the access port, the assembly may be operated to extend the probe downward to retrieve an object (e.g., pill or other medicament). In one embodiment, the probe assembly includes a generally vertical slide channel 864 that has a toothed belt, a toothed slide or similar mechanism therein to which a vertical slide bracket 866 is attached. The slide bracket moves up or down in response to the movement of the belt or slide (not shown), which is itself driven by a vertical slide motor 862. Motor 862 may be a TSM25-075—Permanent Magnet (PM) Stepper Motor from Anaheim Automation. As with the other motors disclosed in the embodiments herein, the motors are of a type suitable to permit control of the motor and thereby the associated position of a device operatively associated with the motor. In this case, it is the slide bracket that has its position controlled by the motor. Also included in the probe assembly 860 are limit switches to detect when the bracket has reached extreme travel positions, as well as a spring-loaded probe column 868 enclosed by a column retainer having a microswitch to detect displacement of the spring-loaded probe column 868 relative to the retainer 872, all of which are operatively attached to bracket 866. The probe column includes a cylindrical tube passing therethrough that is spring loaded in the downward direction to provide some resiliency when the probe head 874 and probe tip 876 come into contact with objects in the bin, or possibly the bottom of the bin itself. Lastly, as depicted in FIG. 7, for example, an object in the form of a tablet 898 has been retrieved and is suspended from the probe tip.

The force necessary to hold the object to probe tip 876 is created by a suction or vacuum applied at the tip. As illustrated in FIGS. 7 and 8, the tip is connected to the hollow cylindrical tube or column 868, and the opposite end of the column is attached via vacuum tubing 810 to a vacuum source such as a vacuum pump 420. Vacuum pump 420 is powered by the same source of power suitable for powering the other components in system 110, and further includes a muffler and associated foam mount to reduce the transfer of vibration to the frame and other components in system 110. The vacuum tubing includes a tee or similar component suitable for splitting off a tubing line that is then connected to a vacuum sensor 460, where the vacuum sensor is used to sense the level of vacuum pressure in the tubing, and thus at the probe tip, and thereby control the level as required and to sense when an item is occluding the probe tip during retrieval and pre-dispense operations.

As noted above, the probe must be able to extend downward into the bin or container in order to retrieve an object such as a pill. Thus, prior to beginning a retrieval operation, the access port 814 must be revealed by moving access port cover 832. As illustrated in FIG. 10A, for example, the port cover is connected to a cover motor 830 via at least one linkage 834. In one embodiment, like the probe slide, a smaller linkage extends from the motor to a pivot on one end of port cover linkage 834, and the opposite end of the port cover linkage is pivotally attached to the port cover 832. As motor 830 is energized in one direction, the linkages pull or slide port cover 832 in the direction generally indicated by arrow 807, revealing the access port 814 and pre-dispense port 816, as depicted in FIG. 10C. When the unattached end of port cover linkage 834 breaks the sensor beam of cover linkage home sensor 838, the linkage is at its maximum travel position and the ports are opened to allow the probe and objects to pass therethrough.

Another feature of the disclosed system is the ability to not only open and close a cover over ports 814 and 816, but to physically release or apply a cover 808 on the tops of all bins on the carousel, referred to as a hurricane cover, and the hubs for controlling the application of the cover are generally illustrated by reference numeral 440 in FIG. 9. As noted herein, such a feature enables the movement, shipping and cleaning of the system without worry that any objects will become displaced from one bin into another or to move about freely in the machine. Moreover, the system includes a backup battery 452 (e.g., 12 v -12 AH battery from Shark) in order to assure that even in the event of a power loss, there is adequate energy so that the system can operate at a low-power mode or at least enter into a locked mode. More specifically, the movement of port cover linkage 834, between the positions illustrated in FIGS. 10A through 10D is similarly represented in FIGS. 12A through 12B. Briefly referring to FIGS. 12A and 12B, port cover 832 is also connected to an outer hub 844 using container cover linkage 840. The movement of the outer hub 844, relative to an inner hub 846, using cams 870 creates a relative up/down motion that is employed to lift or downwardly depress a cover attached to the central hub 846, where the cover fits over the entire top region of all bins on the carousel, thereby applying a complete seal on the containers to assure that no objects are displaced from the bins if the system is moved.

In order to assure that the system may be manually accessed in the event of a prolonged power failure, where the battery backup power is no longer available, the system provides for manual intervention to access the stored medications. To do so, one would first unlock the restocking container key lock 160. Once unlocked, the restocking container 140 is swung open and a small implement (e.g., small pin or screwdriver) is inserted upward through slot 842 and into contact with a cover access lever or "hurricane lever" 836. Then, while maintaining contact with the lever 836, sliding the implement along slot 842 in the direction of arrow 807, and the cover mechanisms described above are manually released. Once released, the carousel may be manually rotated and the bins may be individually removed to access the medications therein.

Figure 12B:
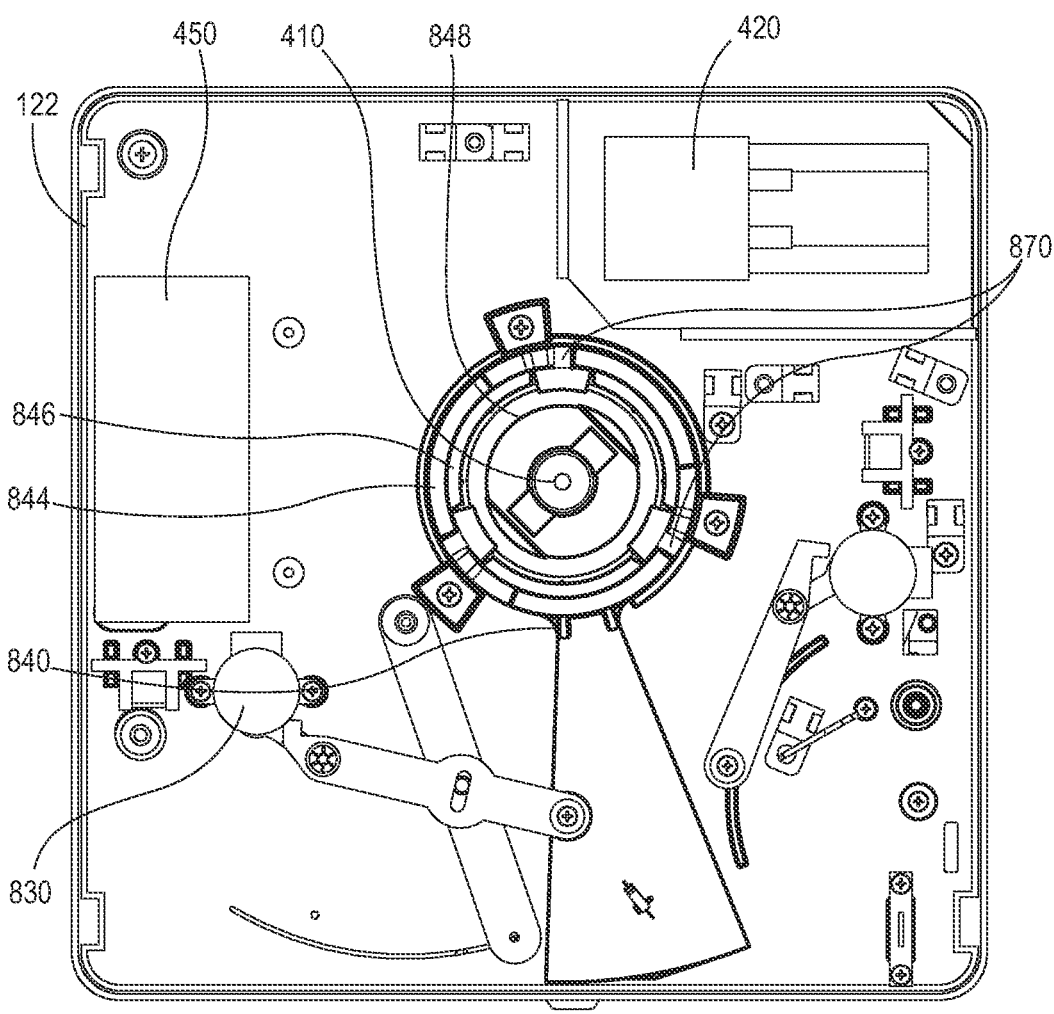
Figure 13:
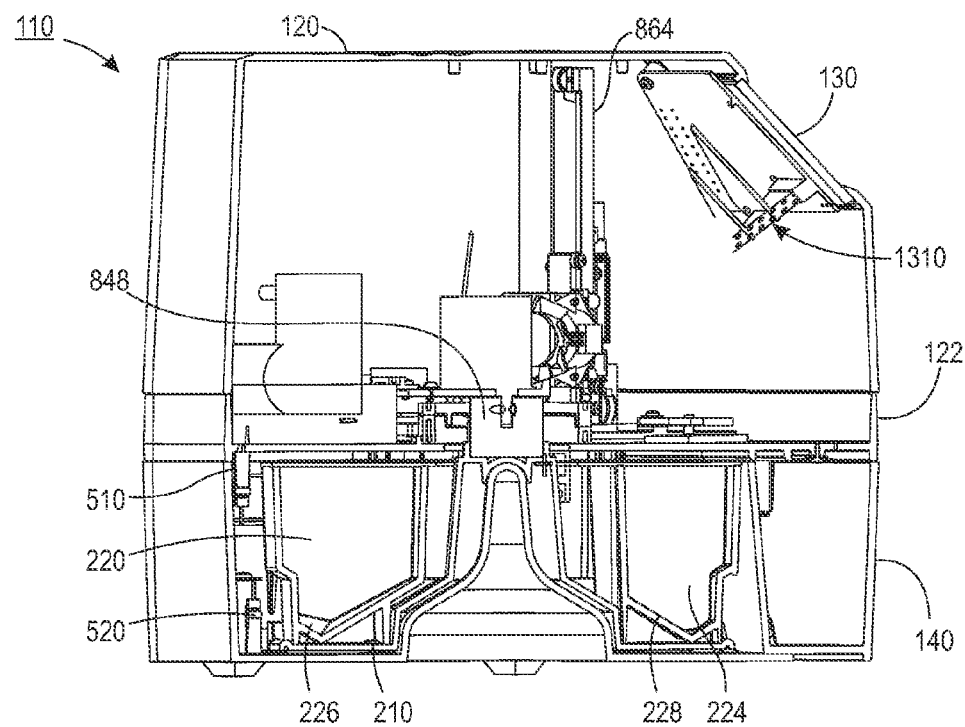
FIG. 13 is a rear cutaway view of the pill dispensing system of FIG. 1.

The rotation and rotational position of the carousel and associated bins is controlled by a carousel rotation drive motor 410. Referring to FIGS. 9 and 13, the position of the carousel 210 is monitored by a reflective sensor 520 that is suitable to detecting a home indicator on carousel 210. Once driven to the point where the home indicator is sensed, the carousel position is then monitored through the drive signals provided to motor 410. In one embodiment, motor 410 is a stepper-type motor available from Anaheim Automation (e.g., TGM42 Permanent Magnet (PM) Stepper Motors with Spur Gearboxes). Motor 410 is operatively connected to the carousel via a transmission 848 (FIGS. 12B, 13). Like the other motors, motor 410 is driven under the control of a motor driver 458 in response to signals from microcontroller 454. In addition to sensing the home indicator for carousel 210, a bin sensor 510 is located above the carousel sensor 520, where bin sensor 510 is suitable for sensing barcodes or similar markings on the outermost surfaces of the bins. The bins may be uniquely numbered, or may be numbered in accordance with the bin size. As with the objects stored therein, the characteristics of a particular bin may be identified based upon the barcode, thereby allowing the system to determine the capacity of the bin merely by the signals generated from sensor 510 as the bin rotates through its sensing region.

Referring briefly to FIG. 10C, as well as FIGS. 7, 8 and 10A, an imaging device such as a digital camera 480 is illustrated in FIGS. 8 and 10C. The camera is used to capture a digital image of the object (e.g., medicament) that has been retrieved by the vacuum probe, and one or more mirrors (e.g., 482, 484) are employed to allow the camera to capture alternative views in a single image. For example, when the retrieval probe assembly 860 is in the retrieval position, the camera is capable of capturing a front view of the object directly, while capturing at least a partial rear view via mirror 482. Then, as the retrieval probe assembly 860 slides outward toward the dispense position (over the pre-dispense port as illustrated in FIG. 8), mirror 484 is in direct view of the camera 480 and the camera may be used to view of capture an image of the bottom of the container lying beneath the access port. In this way it is possible to confirm the type of object retrieved and/or confirm that there are objects or pills remaining in the bin. As will be appreciated, the use of a camera(s) and mirror(s) would enable the acquisition and storage of an image for each dispensed pill and/or retrieval event. For example, an image of the dispense cup could be taken before and after dispensing to the user, to confirm the items dispensed, and that all items were actually dispensed. Such a capability would permit creation of an audit trail for all dispense events, inventory, meds schedule, messages, all user menu choices, caregiver menu choices, and even what happened in case of any type of system error or operator error.

Referring also to FIGS. 11A and 11B, when the retrieval probe assembly is moved into the horizontal retrieval position and the access port is open, the probe retainer 872 and column 868 is extended into a bin 224, at which time the vacuum pump is energized and air is drawn up through tip 876 to create a vacuum and cause a suction force intended to attract at least one pill 898. A probe micro-switch 878 is triggered whenever the probe tip comes into immovable contact with a surface such as an object or container surface. Whenever the switch is tripped without a preceding change in vacuum pressure, the retrieval attempt is aborted and the process restarts. A pressure transducer (or other types of sensor and circuit) provides feedback to detect negative pressure when at least one pill 898 has been "gripped" by tip 876 of the retrieval probe. Upon detecting the change in pressure, the probe retainer is retracted so that the pill is retrieved and suspended above the access port. At this point one or more singulation techniques may be employed to assure that only a single pill or object is removed from the bin. If singulation is confirmed, the retrieval and dispense process would continue as pill 898 is then moved by advancing the retrieval probe slide to the pre-dispense position.

This process of selecting pills from individual bins or containers (e.g., 220, 224) is repeated until all the objects for a scheduled dispensing period are collected into the associated temporary pre-dispense receptacle 310. This pre-dispense step is complete once all required medications have been staged for the next dispensing time and is subsequently released when the patient indicates they are ready for the dose, via the pre-dispense receptacle into dispense cup 150, for their consumption in a timely manner. In the case where the patient forgets to retrieve the prescription medications from system 110, the pills are moved to a restocking cup or container 140 for future restocking and the information is stored in the data or log file so that subsequent doses can be adjusted based on preprogrammed protocols and a message may be sent to the patient's designated care giver or health care provider for remedial action.

It should be further understood by those skilled in the art that, in lieu of using a vacuum tip 876 for retrieval, a mechanical claw-like grappling device, that physically grips a selected object, or an adherent coating (sticky substance), electromagnetic attractor (especially for metallic objects) or similar 'gripping' component, could be used and may even be interchangeable with tip 876. The appropriate structure and form factor of the retrieval probe will depend upon the physical attributes of the medicament, preferably a pill, tablet, or capsule, but it may also be a packaged medicine, vial, ampoule, bandage, dressing or other object. Therefore, given the range of sizes and shapes, the retrieval mechanism may need to have a positive gripping means that can be adapted to handle a variety of types of objects. It is further understood that such a gripper could be actuated in a variety of ways including pneumatically or with a motor or solenoid. In addition to the probe assembly 860 depicted in the figure discussed (e.g., FIG. 8, an alternative probe embodiment is also contemplated as illustrated, for example, in FIG. 19. There a flexible vacuum tubing 810 is employed that travels within a sheath 815 under the control of a plurality of drive and idler rollers 817 and 819, respectively, that do not pinch the tubing off but apply adequate driving force to extend and retract the probe through the sheath 815.

Figure 14:
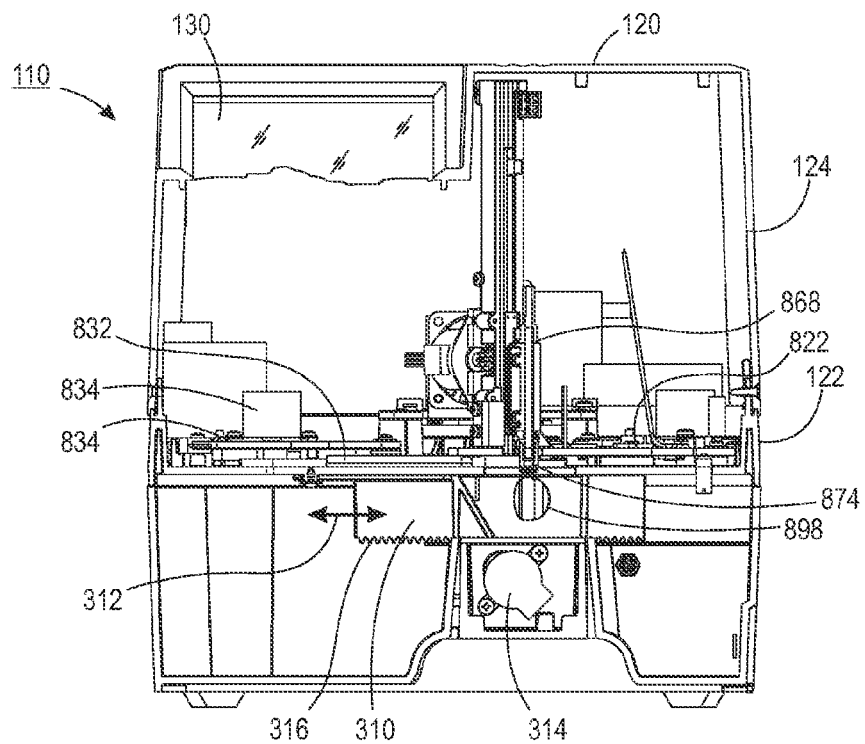
FIG. 14 is a front cutaway view of the pill dispensing system of FIG. 2.
Figure 15:
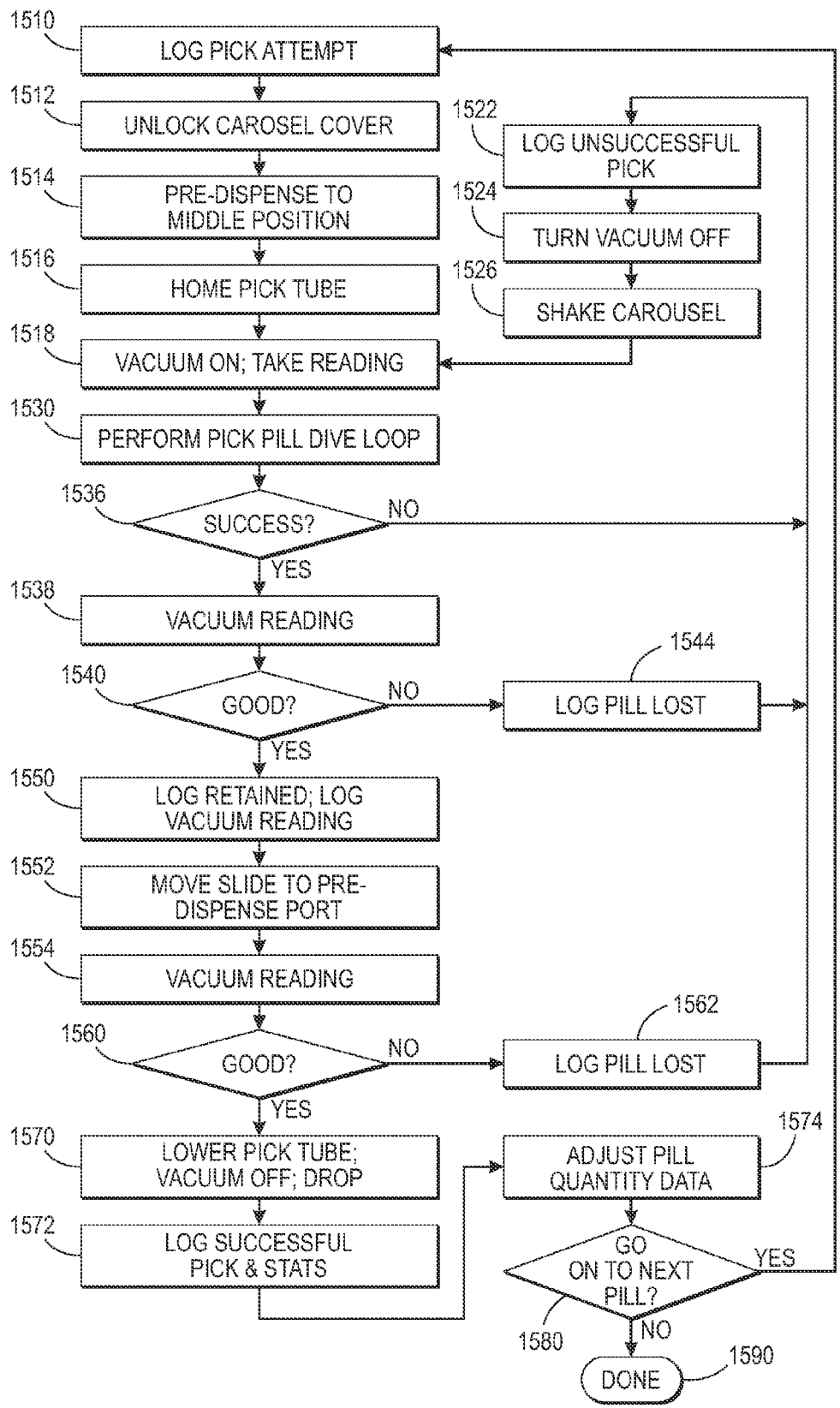
FIG. 15 is a flowchart illustrating various operations in a picking method in accordance with an aspect of the disclosed embodiments.

Having described the various components of the basis dispensing system, attention is turned to the operation of the system, with a particular example of a retrieval process as represented in the flowchart of FIG. 15. Starting with the components in the positions represented in FIG. 10A, the system would execute a dispensing operation as follows. First, as illustrated by 1510, the system would initiate a record in the log to track the pick or retrieval attempt. Next, the carousel cover is unlocked at 1512, as described above to permit the rotational movement of the carousel and associated bins. To prepare for receipt of a retrieved item(s), the pre-dispense receptacle and slide 310 are moved to a central or pre-dispense position as represented in FIG. 14, where the pre-dispense receptacle is below the pre-dispense port. Movement of the pre-dispense receptacle is accomplished under the control of pre-dispense slide motor 314 (e.g., TGM24), which acts on the toothed slide 316 to move the receptacle 310 in the horizontal direction indicated by arrow 312. As represented by operation 1514, the pre-dispense receptacle is moved to a middle or central position between the dispense cup and restocking container, where a flat bottom provides a repository for medicaments prior to their being dispensed.

Next, the retrieval assembly and retrieval probe are moved to a home position, operation 1516, and the vacuum pump is turned on at 1518. The pressure reading in the vacuum tubing is stored and then a pill pick or retrieval loop is initiated. The loop 1530, as generally described above, initiates the downward extension of the probe until either a change in the vacuum pressure is detected or the retrieval probe column retainer micro-switch is tripped indicating probe contact. The probe is then retracted, at least partially and in the event that the vacuum pressure remains at an increased level, a pill is assumed to have been retrieved. The successful retrieval, as tested at 1536, would see the vacuum pressure remain at the increased level and may further confirm that an object has been retrieved through the use of visual analysis using camera 480 as briefly described above.

If a pill has not been successfully removed, the process would continue at 1522, where the unsuccessful pick loop is recorded, the vacuum is turned off (1524) to assure that any debris attracted to the probe tip 876 is allowed to fall back into the bin. The carousel is then shaken, vibrated or otherwise moved at 1526 in order to attempt to shift or move items remaining therein before reinitiating the retrieval loop. It will be appreciated that various alternative methods or mechanisms may be employed to attempt to improve the likelihood of pill retrieval, including slight movement of the carousel while the probe is in an extended downward position in order to disturb any agglomeration of medicaments. Also contemplated are movable bin bottoms or portions thereof, bladders and other mechanical solutions to assure objects move to a centralized pick position in a bin. One method contemplated herein is the use of a "search" or "dithering" pattern for relative motion between the probe tip and the bin. In other words, rather than try to reliably move objects to the pick location, the system varies the pick location when an initial attempt is unable to successfully retrieve an object.

As a result of both the retrieval probe slide and the carousel being rotational motion systems, which are not aligned on a common axis, the process of moving the probe relative to the bin requires control of both the position of the probe and of the carousel. If one considers the operation as moving based upon vectors, the dithering operation may be expressed in the programmatic code segment as follows:

```
#define N_DITHER_POSITIONS 21
// the pivot for the pick slide is off-axis,
// and while we have a good approximation by doing a 3x3 grid,
// we have a couple extra opportunities at the back of the bin at 0,2 and 1,2
// if we did it at -1,2 we would move the carousel :(
float standardDitherPositions[N_DITHER_POSITIONS][2] =
{
    // change in carousel, change in pick slide
    { 0, 1 }, // try dead center first
    { 0, 2 }, // try dead center towards back
    { 0, 3 }, // try dead center towards back
    // left side group (looking from above)
    { 1.1, -1.3 },
    { 1.1, -.8 },
    { 1.2, 0 },
    { 1.2, 1 },
    { 1.2, 2 },
    { 1.2, 3 },
    { 1.2, 4 },
    // middle group
    { 0, -1.5 },
    { 0, -1 },
    { 0, 0 },
    { 0, 1 },
    { 0, 2 },
    { 0, 3 },
    // right side group (looking from above)
    { -1.2, -1.5 },
    { -1.1, -1 },
    { -1, 0 },
    { -.9, 1 },
    { -.8, 2 }
};
#define SMALL_PILL_DITHER_COUNT 32
float smallPillDitherPositions[SMALL_PILL_DITHER_COUNT][2] =
{
    // change in carousel, change in pick slide
    { 0, 1 }, // try dead center first
    { 0, 2 }, // try dead center towards back
    { 0, 3 }, // try dead center towards back
    // left side group (looking from above)
    { 1.1, -1.3 },
    { 1.1, -.8 },
    { 1.1, -0.5 },
    { 1.2, 0 },
    { 1.2, 0.5 },
    { 1.2, 1 },
    { 1.2, 1.5 },
    { 1.2, 2 },
    { 1.2, 2.5 },
    { 1.2, 3 },
    { 1.2, 3.5 },
    // middle group
    { 0, -1.5 },
    { 0, -1 },
    { 0, -0.5 },
    { 0, 0 },
    { 0, 0.5 },
    { 0, 1 },
    { 0, 1.5 },
    { 0, 2 },
    { 0, 2.5 },
    { 0, 3 },
    // right side group (looking from above)
    { -1.2, -1.5 },
    { -1.2, -1 },
    { -1.1, -0.5 },
    { -1, 0 },
    { -.9, 0.5 },
    { -.9, 1 },
    { -.8, 1.5 },
    { -.8, 2 }
};
```

Notably, the dithering vectors (table) may be modified based upon the size of the respective bin. Empirical evidence suggests that the dithering or searching strategy employed generally produces a successful result after only one or two additional tries and seldom, if ever, ends up sampling all of the various locations that are possible unless the bin is almost empty. Another possible option for retrieval retries is an adjustment of the vacuum pressure level. For example, after several tries to retrieve a pill or object that may be heavier, the system may increase the vacuum pressure applied to the retrieval tip, thereby increasing the force that the tip is capable of applying to the object.

Continuing with FIG. 15, in the event of success at 1536, the vacuum reading is again sampled at 1538, and then tested against the stored vacuum data at 1540 to determine if the pill remains attached to the probe. If the outcome at 1540 is No, the pill is determined to be lost, the lost pill even is logged at 1544, and the process continues at 1522 where the pill is logged as lost upon retrieval. It is further noted that the vacuum pressure readings may be averaged or smoothed over a series of readings, and then analyzed or compared with respect to a tolerance for variation in order assure that anomalies do not impact the operation of the system.

If the pill was successful retrieved, the vacuum reading taken at 1538 is logged, the pill is indicated as retained, as represented by 1550 and the pill retrieval apparatus slides over to the pill dispense position 1552, for example as represented in FIG. 10D. Once in the pre-dispense position the vacuum reading is again taken to assure that the pill was not dislodged from the probe tip while sliding. Again, in the event that the vacuum reading shows a decrease, the pill is determined to be lost and the log is updated to indicate that the pill is lost at 1562, before restarting the retrieval process.

Assuming a successful reading at 1554, and the test at 1560 is satisfied (i.e., no change in pressure), the process continues at 1570, where the retrieval probe is lowered slightly to assure that the pill will fall into the pre-dispense receptacle, and then the vacuum is turned off, thereby releasing the pressure holding the pill to the probe tip. The pill then drops into the pre-dispense receptacle as reflected in 1570, a successful retrieval is logged and the statistics, and possibly an image, of the successful retrieval are logged at 1572 before the pill quantity (inventory) is adjusted at 1574. Once successful, the process either repeats for additional pills to be readied for dispense at 1580, or continues to completion at 1590, where the system then awaits an affirmative response from the user in order to slide the pre-dispense receptacle to the right and empty the collected pills or objects into the dispense cup 150 for retrieval.

As will be appreciated, certain of the operations may be performed slightly in advance of a scheduled medication tie in order to ready the pills for dispensing at the designated time. The system would collect the necessary medicaments and then signal the user (visually and/or audibly) that the medication is ready for dispense. However, unlike other systems, the medications are not actually dispensed until there is an affirmative confirmation from the user. Thus, in the event that the medications that are queued for dispensing in the pre-dispense receptacle are not retrieved, the pre-dispense receptacle can be slid to the left and the medicaments are transferred to a restocking cup to be later manually restocked in the appropriate bin(s).

Turning next to FIGS. 16A-16G, depicted therein are a series of user-interface screens that generally illustrate various functions and features of an embodiment of the dispensing system. As illustrated in the main menu screen of FIG. 16A, the interface 130 presents, under the programmatic control of microcontroller 454 and/or a video display controller 1310, a plurality of selection options including as needed medication (1612), early distribution of medications (1614), a late distribution of medications or missed dose (1616), and an ability to review the medication schedule (1618). The system also provide an administrative or "caregiver" access capability that allows the caregiver to both interface and adjust the schedule, dosages and the like, but also allows the caregiver to access the machine to fill, refill and restock medicaments.

Figure 16A:
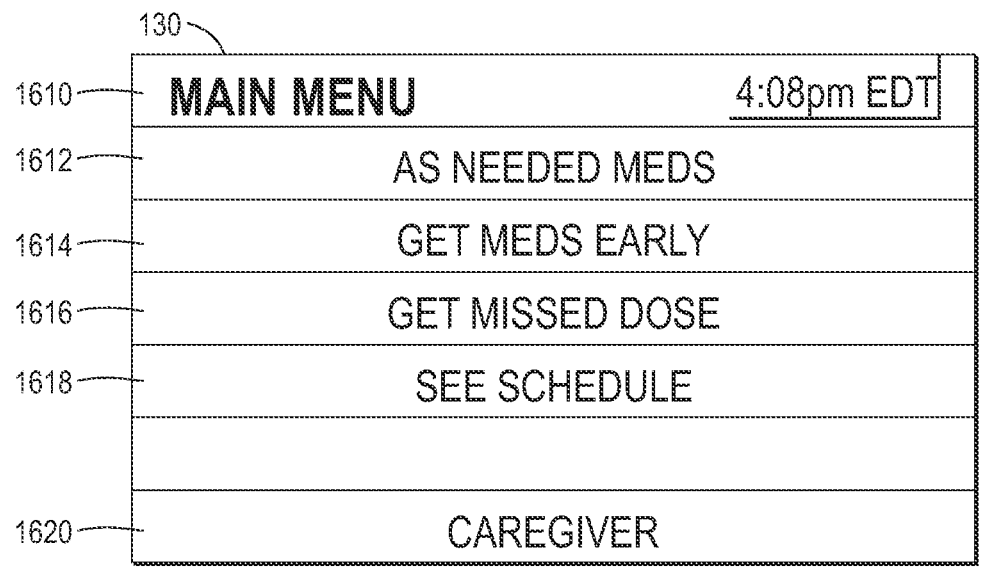
FIGS. 16A-16H are a plurality of exemplary user-interface screens in accordance with an aspect of the disclosed embodiments.
Figure 16B:
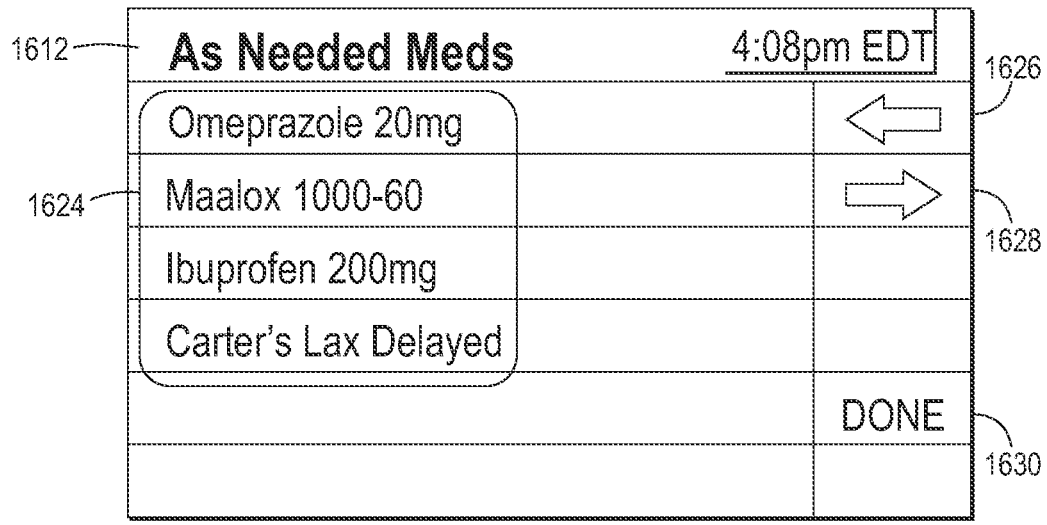

FIG. 16B is presented in response to a user's selection of item 1612 in FIG. 16A. Menu screen 1612 provides, in region 1624, a listing of the medication stocked in the dispensing system that may be dispensed on an as-needed basis to the user. To initiate such an action, the user would make a selection of the particular medication and would then press the forward arrow key 1628 to continue. For ease of navigation, arrow keys 1626 and 1628, or similar prompts and icons may be used to facilitate a user's interaction with the dispensing system via interface 130. In response to a completed as-needed (PNR) request, the system would proceed through the dispensing sequence described in detail above to provide the requested medicament via dispense cup 150.

Figure 16C:
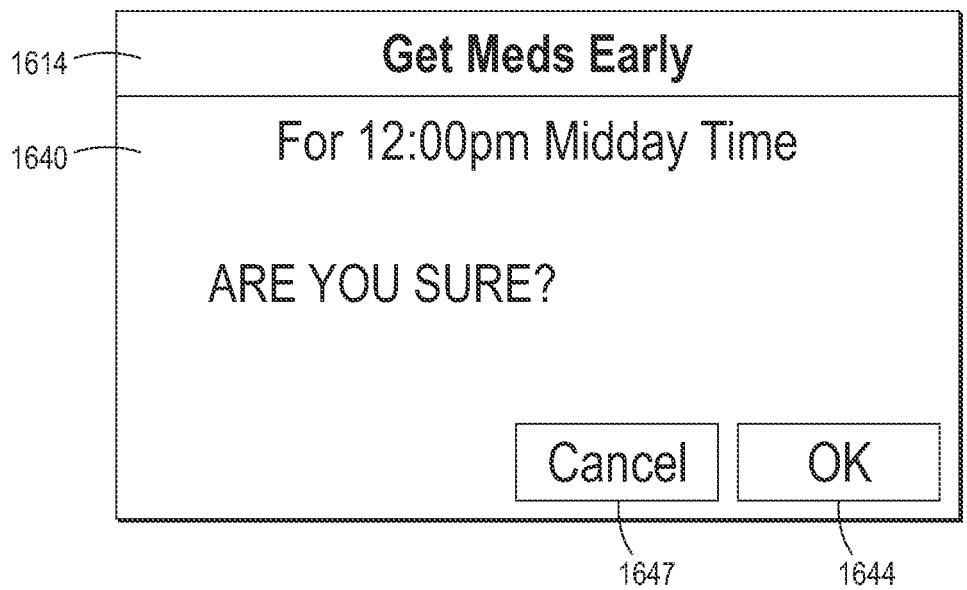

In response to a user selection of item 1614 in FIG. 16A, the screen of FIG. 16C would be presented. The menu screen for the "get meds early" selection provides for a user's confirmation of the request. In addition to presenting the cancel (1647) and OK (1644) options, region 1640 also identifies the next scheduled dosage or dispense time for the user to confirm. It will be appreciated that alternative messages may be displayed at this point, or in the event of the next scheduled dispense being a dosage that cannot be taken early, the system might require a caregiver override or additional interaction.

Figure 16D:
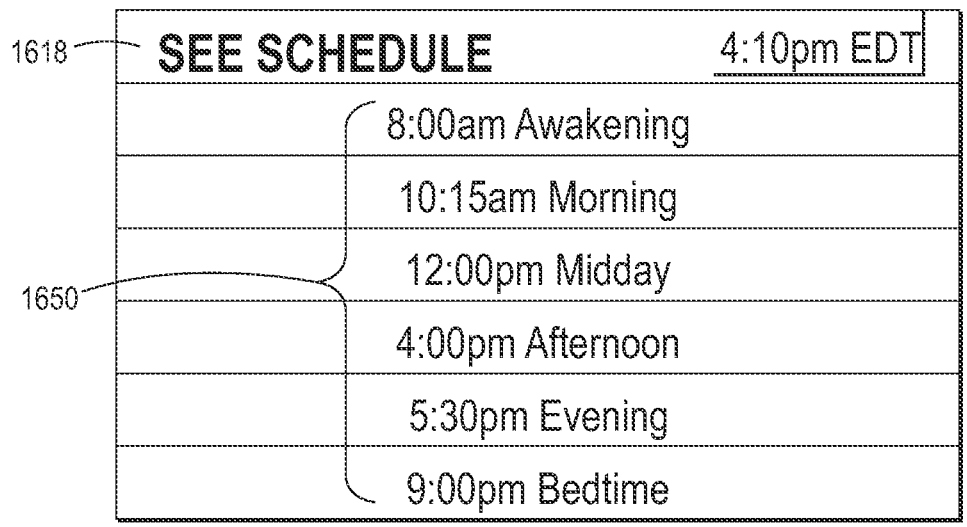

User selection of the "see schedule" option 1618 in FIG. 16A results in the presentation of the interface screen of FIG. 16D, whereby a user is presented with the dispensing schedule times in region 1650. Selection, at this level would result in the particular dispensing data being displayed, including information such as the medication, the dosage amount, as well as any additional instructions (e.g., take with food, take after eating, etc.).

Figure 16E:
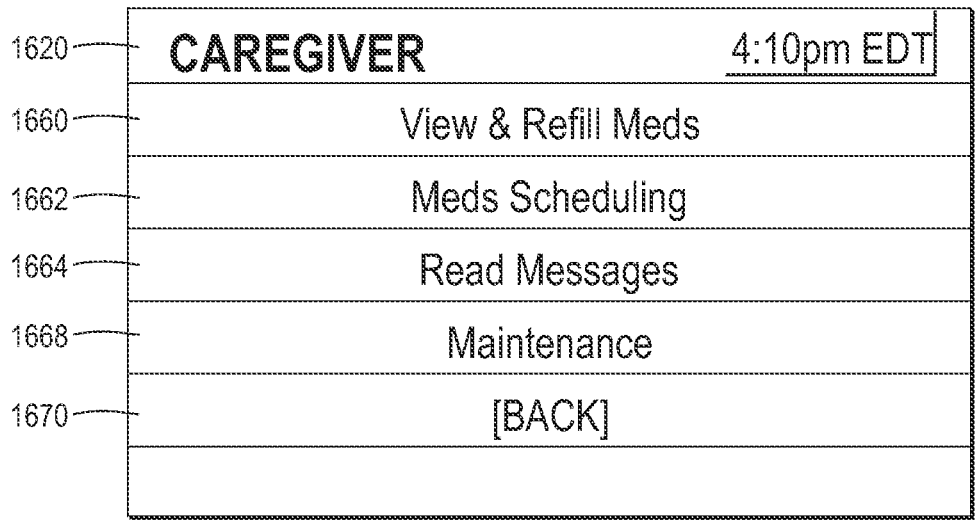
Figure 16F:
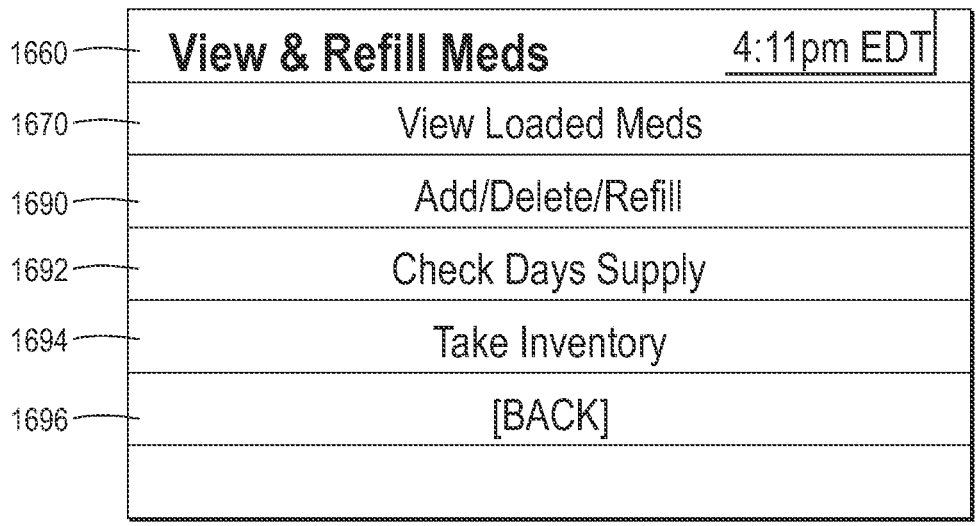
Figure 16G:
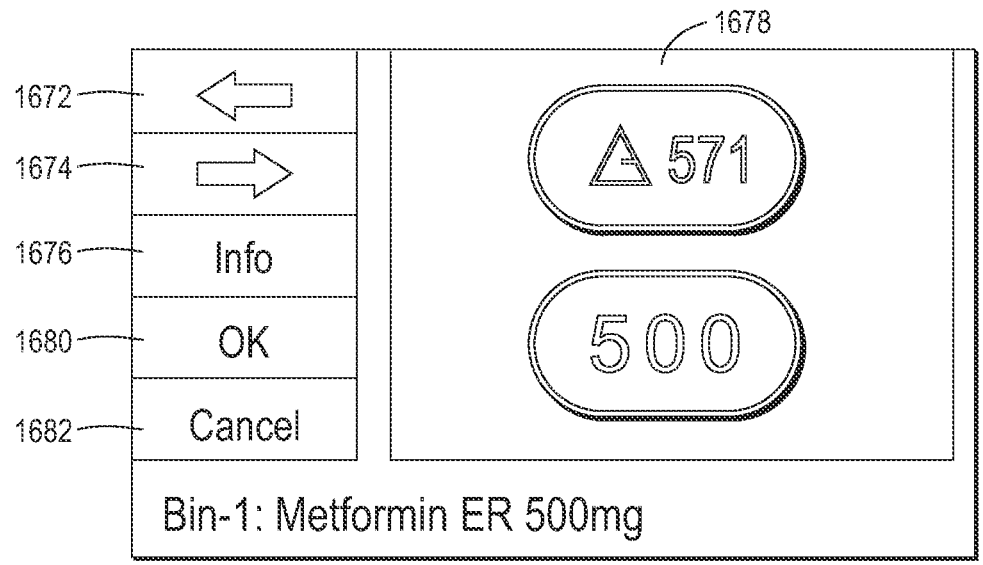
Figure 16H:
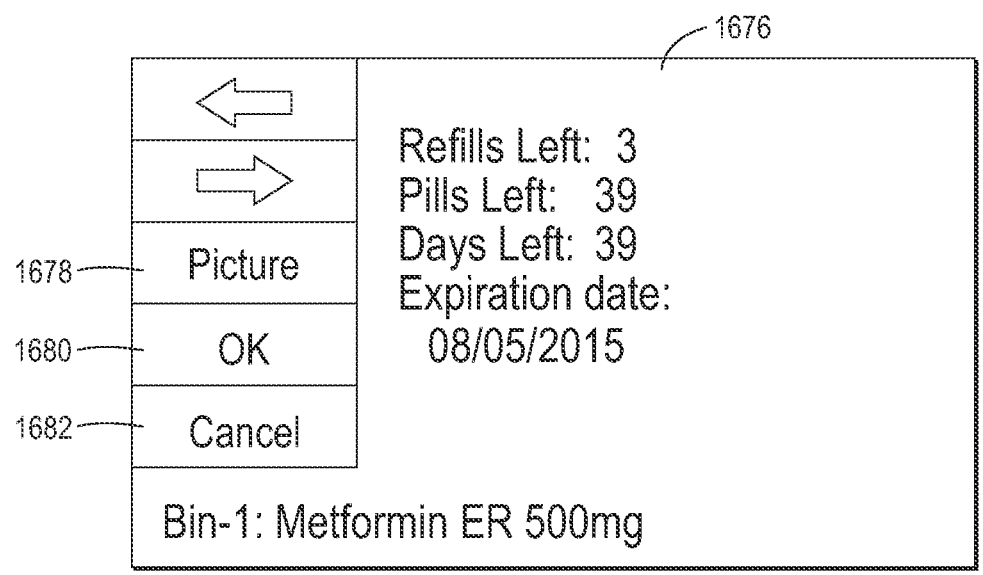

The caregiver selection on the interface display of FIG. 16A leads to a series of additional menu options as depicted in FIG. 16E. The caregiver screen 1620 includes selections such as: view & refill medications (1660), medication scheduling (1662), messages (1664), maintenance (1668) and a navigation or "back" selection 1670. As illustrated in FIG. 16F, the view and refill medications selection 1660 allows the caregiver to review loaded medications (1670), add, delete, or refill medications (1690), check the number of days of supply for each medication (1692) and an inventory option (1696). These options are believed to be self-explanatory, although the view loaded meds option 1670 results in the display of an interface screen such as that depicted in the example of FIG. 16G. In the figure, arrows 1672 and 1674 allow for the caregiver to navigate through each of the medicaments that are programmed in the machine, and for each medication a picture or iconic representation of the medication is provided in region 1678 to facilitate identification of the medicament. A selection of the info option in 1676 results in detailed information about the medicament as depicted in FIG. 16H, including dosage, number of refills, etc. may be included in the displayed information available to the caregiver. The interface further provides a selection to accept the information and continue (1680), or to return to the prior menu via a cancel option 1682. Thus a caregiver may scroll or move through or alternate between detailed information in region 1676 of FIG. 16H and the picture or icon representation of the medication depicted in region 1678 of FIG. 16G.

Having described in detail an embodiment of the dispensing system and the method of operating the system, attention is now turned to the further description of several alternative and additional embodiments, some of which have been generally described above. For example, referring to FIGS. 17 and 18, depicted therein are alternative designs for a variable orifice that may be used as one type of singulator in accordance with the disclosed system.

Figure 17:
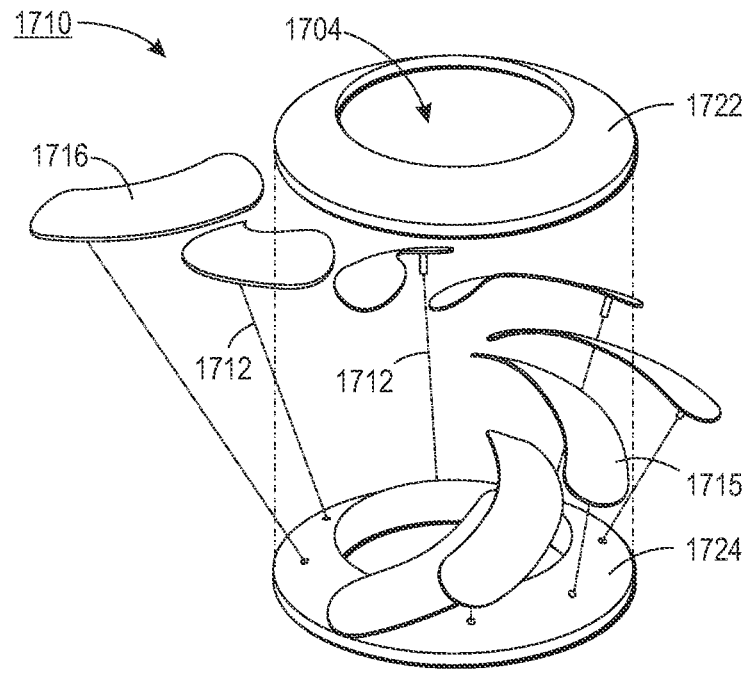
FIG. 17 is a perspective assembly view of a variable orifice in accordance with an alternative embodiment.

As illustrated in FIG. 17, for example, variable orifice 1710 is interposed between the pill retrieval mechanism and the objects in the container (220, 224), such that the distal end of the probe, with tip 876, passes through orifice 1704. As retrieval probe 874 begins to retract to the distal end of the probe may have one or more pills 898 attached as a result of the vacuum or other gripping means discussed above. More than one pill may be gripped as a direct effect of the gripping means or because pills are adhered to each other. As the probe is retracted through the orifice 1710, the size of the orifice aperture 1704 is such that only a single pill is permitted to pass through and exit the variable orifice. If more than one pill is gripped by the probe, the extra pill(s) will be dislodged or all of the pills will be dislodged and fall back into the storage container (220, 224). The process can be repeated until a single pill successfully passes through the orifice 1704 and can subsequently be move to the pre-dispense receptacle 310.

The adjustable diameter of orifice 1704 reduces the possibility of having more than one pill being acquired by probe tip 876 at a time. However, there remains a possibility of dislodging the gripped object (e.g., pill) when the aperture is sized to permit only one item to pass through. To reduce the likelihood of dislodging the gripped object, the embodiments described below may further include a taper or conic portion leading to the opening in the orifice as facilitated by the conically-shaped sections 1715 and 1716 as depicted. Moreover, like a camera iris, movement of the retaining rings 1722 and 1724 relative to one another will cause an adjustment in the aperture size. Movement of a gripped item through the taper tends to align or shift the object so as to "center" it relative to the tip and thereby reduce the likelihood that it will be dislodged as it passes through the orifice. As will be further described below, the size of the orifice opening will have been previously adjusted to an optimum opening for the specific pill or object to be retrieved, thereby assuring singulation Continuing to refer to FIG. 17, the conical orifice includes a mechanism to control the size of orifice opening 1704. In one embodiment, the mechanism comprises a plurality of blade elements 1715, 1716, each mounted on fulcrum pins 1712, inserted into proximal and distal blade rings 1722 and 1724 respectively. As the blade retainers are rotated relative to one another, the blade elements are caused to rotate about their respective fulcrum pins 1712 and, as a function of their specific profile, form a generally circular yet variable-sized orifice. Each of the blades 1716 is either pre-curved and/or flexible so as to adopt the curvature imposed thereon by the blade retainers. Moreover, as with a conventional iris-adjusting mechanism (controlling the size of the orifice 1704), the orifice may be adjusted from essentially full closure to a diameter that is slightly less than the inner diameter of blade ring 1722. As noted, such functionality is similar to that used for an iris in photographic equipment, albeit different as the disclosed orifice has a cone-shaped or tapered lead-in to the orifice. As suggested above, the tapered feature is an improvement over a planar orifice (typical of a photography iris) since the conic nature of the collective blade elements 1716 facilitates the alignment of an object on the probe tip 876 and retrieval of only a single object (e.g. pill). The mechanism to control operation and size of the orifice, by moving ring 1722 relative to ring 1724, is not shown, but can consist of a variety of motorized or similar electromechanical devices suitable for causing relative movement between the retainer rings.

Figure 18:
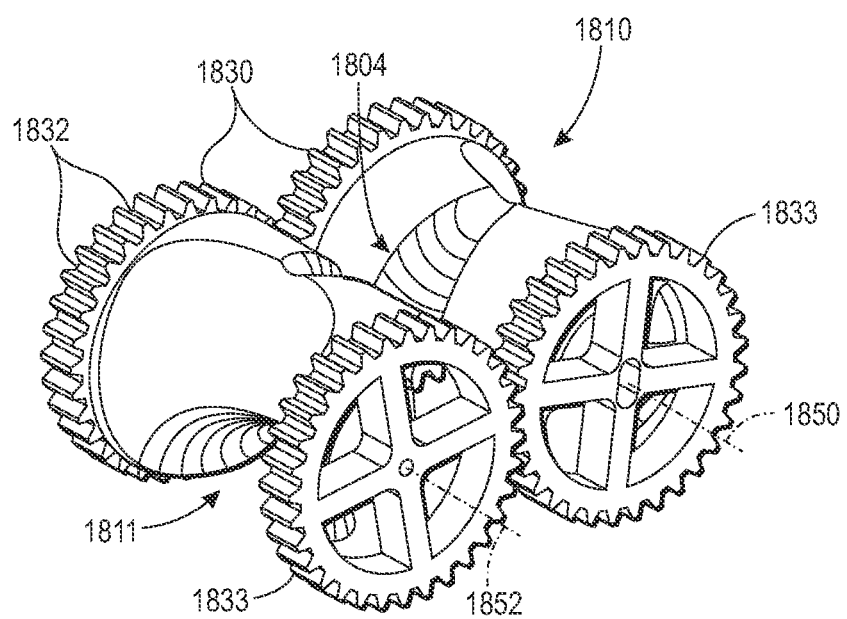
FIG. 18 is a perspective view of an alternative variable orifice in accordance with an alternative embodiment.
Figure 19:
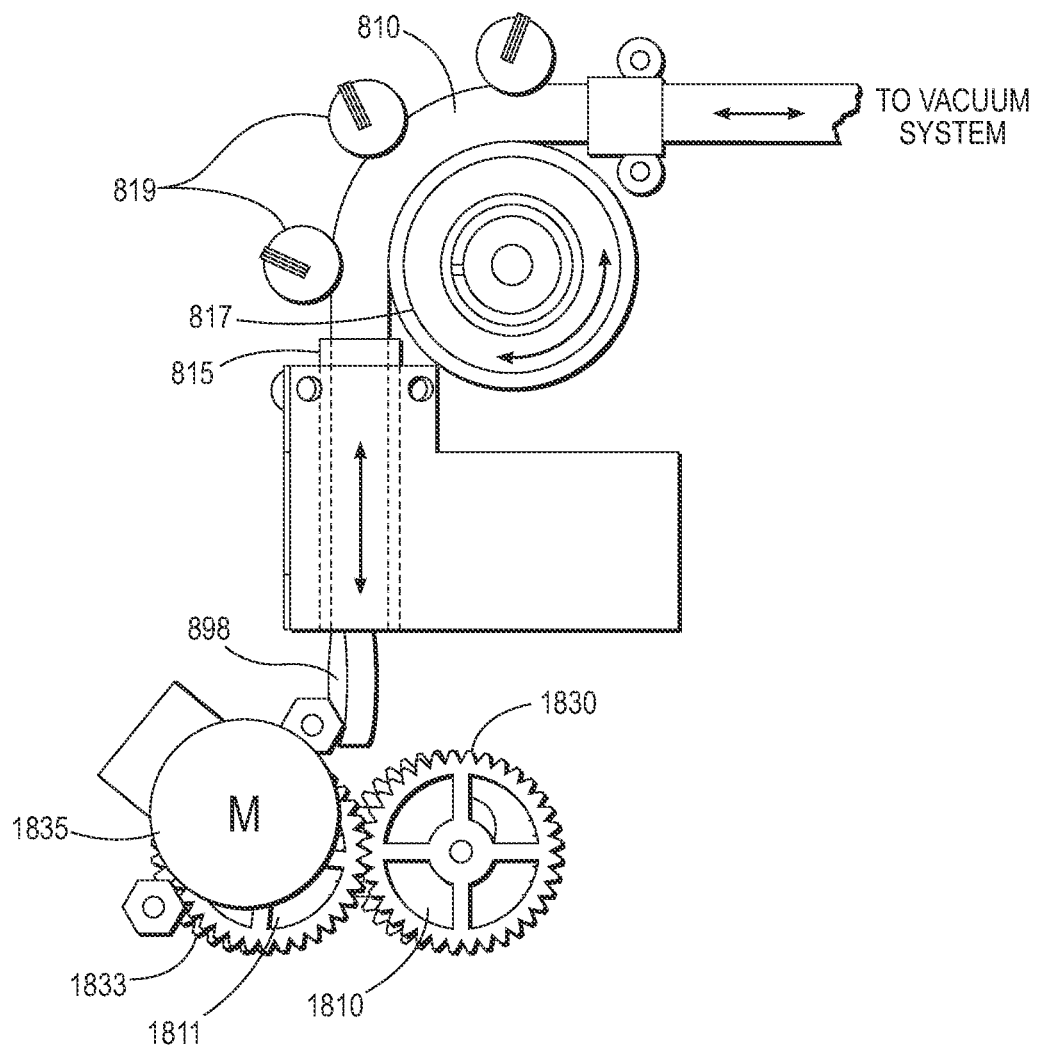
FIG. 19 is a partial view of a vacuum probe and variable orifice in accordance with an embodiment of the dispensing system.

Turning next to FIG. 18, shown therein is a perspective view of an alternative embodiment for providing a variable orifice, whereby the variable orifice is created using at least two opposed rollers or elements having a cam-shaped profile. The geometry of the channel leading into orifice opening 1804 is a curvilinear surface having an equiangular spiral surface that defines the size (e.g., diameter) of the opening (1804). Note, this may also be represented as a logarithmic spiral represented by the polar equation r=ae^(bθ). The spiral profiles of the opposed segments 1810 and 1811 further adjust (e.g., decrease) the orifice size as the segments are rotated about the respective axes 1850 and 1852. The advantage afforded by this variable orifice is shown in FIG. 19, where in addition to the cross-section of the roller segments, a probe is displayed to show retrieval of a pill 898. In FIG. 19, a gap or orifice 1804 is sized to only allow the passage of a single pill, thereby enabling singulation of the pills or other objects being retrieved through the orifice.

It will be appreciated that such a channel can be at least approximated by making a series of cuts through rollers 1810 and 1811 along a cutter axis that is perpendicular to the roller axes, and tangent to the surface of the rollers. For each cut in the series of cuts (e.g., cylindrical cuts, although other shapes may be contemplated based upon the items to be singulated), the cutter diameter is decremented or incremented as the rollers 1810 and 1811 are indexed through a small angle about axes 1850 and 1852, respectively. The completed series of cuts creates an aperture groove or channel on the face of the rollers. When viewed from directly above the aperture rollers 1810 and 1811 effectively create a nearly circular orifice 1804 therebetween. It should be appreciated that any of a number of machining techniques may be employed to produce the channel as illustrated. As an alternative to sequential series of cuts as mentioned above, it may also be possible to produce a continuously-varying surface. Provided that a control mechanism can properly control the orientation of rollers 1810 and 1811 relative to one another, the use of a continuously-variable channel surface (no aperture grooves) would essentially result in a means of providing a variable orifice that could be adjusted to any dimension within the range of the sizes available.

As illustrated in the embodiments of FIGS. 18 and 19, when roller 1810 is mated, in phase, to roller 1811 a generally circular orifice is formed therebetween. To assure that the rollers remain mated, in phase, gears 1830 and 1833, and more particularly gear teeth 1832 may be added to one or both ends of each aperture roller, or to axles passing along the axes of the rollers. The gear teeth mesh when rollers 1810 and 1811 are positioned to form an aperture, and allow the roller pair to be actuated by a single driving mechanism such as a motor 1835. In another alternative embodiment, a toothed-belt (not shown) may be employed to link the gears associated with each of the rollers and thereby assure that they rotate in a synchronized manner. It will be further appreciated that the rollers may be synchronized using other techniques as well.

Having described the various features and general functionality of the mechanical singulation embodiments, attention is now turned to the operation of the system in accordance with various methods enabled by the embodiments disclosed. Two general operations may be performed to assure the singulation of objects being retrieved via the variable orifice. In the first operation a dynamic sizing methodology is employed to empirically determine the appropriate orifice size setting for a particular object. In a second, operational, methodology, the variable aperture mechanism is employed to dynamically control the orifice size to assure singulation; for example open large enough to permit a single object to be withdrawn, but closed as the first object is being removed to assure no additional objects (e.g. attached in tandem, to the bottom surface, of the primary object) are retrieved.

Figure 21:
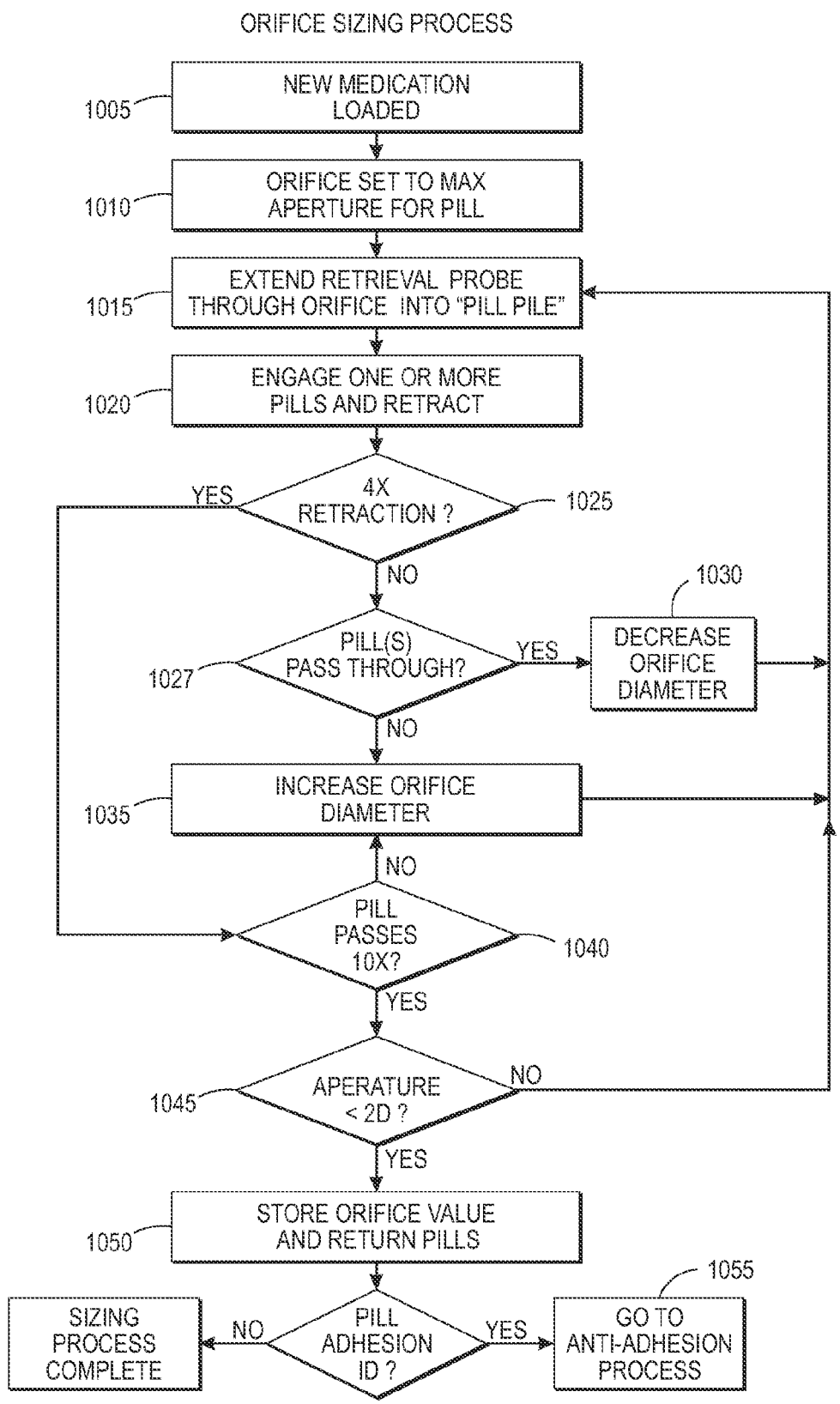
FIGS. 21 and 22 are flowcharts depicting exemplary operations in accordance with the variable orifice apparatus illustrated in FIGS. 17-19.

FIG. 21 depicts an operational flow chart of a process that may be employed for pre-determining the diameter of a variable orifice for a specific object form factor (e.g., pill shape and size). The concept is to identify the minimal orifice diameter to fit the middle dimension of the pill. This is typically the first process performed once a new set of objects (e.g., medications) is added to the system.

Starting with step 1005 a new supply of pills or other objects is bulk loaded into a specific storage container. The algorithm provides for adjustable orifice size setting to determine an orifice size guaranteeing that only one pill (object) at a time is picked from the specific bulk container and transferred to the associated temporary storage container. The variable orifice is first adjusted to an almost maximum opening in step 1010, just prior to retrieval probe being inserted through the variable orifice (step 1015) to engage and remove at least one pill in step 1020. It will be appreciated that something other than the maximum size of the orifice may initially be employed to speed this process, and if no object is retrieved, the process may re-initiate with a larger or maximum size orifice. Step 1020 further includes setting the vacuum probe to a high enough level to pick up at least one of the largest sizes pills that the system and orifice can handle. Determination of whether a pill is present or "gripped" as the tip passes through the orifice is indicated by a release of suction (assessed by airflow, sound, voltage, or other meter in the vacuum system).

A series of attempts (e.g., 4×) then attempt to retrieve a pill through the orifice (Step 1025). If all pills are removed as they pass through the orifice (indicated by release of suction) after several attempts the orifice size is increased by one size (e.g. 0.5 mm diameter) at step 1035. If a pill passes through (1027), the size of the orifice is decreased by one size as indicated at step 1030 until on several attempts no pills traverse the orifice (negative result from test step 1027). Next the orifice is re-opened to the slightly larger size at 1030 allowing a pill through. This orifice size or iris setting is determined as adequate for one pill and the process is repeated at smallest orifice size that a pill successfully made it through to determine frequency of pill traversal of the orifice. For example, if the frequency of completed retrieval is rare (e.g. less than one in ten attempts as represented by step 1040), the next largest orifice size can be tried. In one embodiment, as represented by step 1045, the process of trying the next size can be repeated until adequate frequency of pill passage (but the orifice must be less than twice the diameter of the smallest orifice size that allowed pill passage).

It will be further appreciated that it may be possible to use an orifice diameter just under two times the minimal diameter that will still assure only one pill, unless the pills are adherent in vertical (tandem) dimension or adherent in the narrowest dimension which is less than half a middle dimension. It will be further appreciated that additional techniques may be employed to decrease the likelihood of adherent objects (e.g., shaking or jogging the tip or the retrieval system slightly). Once the orifice size is determined, as represented by step 1050, the orifice setting is stored for the specific objects in a specific bulk container from which the pills were being retrieved. This setting will be used as the pre-determined setting for subsequent retrieval from that container until a reloading of the system initiates a "recalibration"

Figure 22:
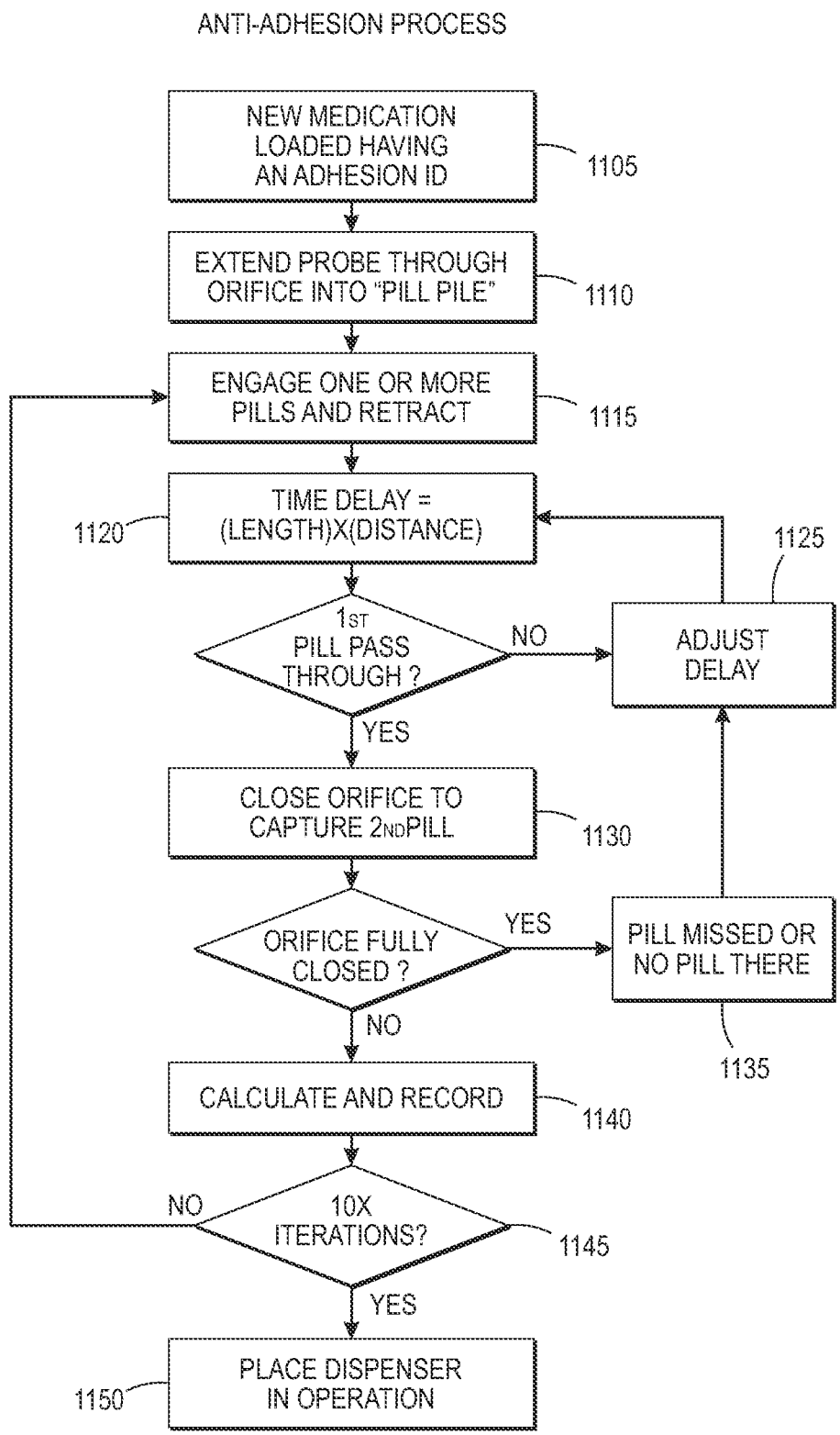

The second process noted above can use vertical 'clamp closure' of the orifice to eliminate pills adhered along a vertical dimension (as the pills are being passed through the orifice). Such a process may also be used in conjunction with a digital imaging system, to facilitate singulation by stripping or clamping other than the first object retrieved. An example of such a process is illustrated in FIG. 22, but it should be appreciated that such a process may not be necessary for objects that do not adhere. To assure that two pills are not adhered in a vertical direction (which may be along smallest diameter when middle and largest diameter are equal for example a tablet shape) the orifice is closed, at least slightly, after the probe tip has passed through the orifice and traveled a certain distance allowing the single primary pill to travel through the opening but not a vertically adhered pill. At a point as the orifice closes it thereby grabs any adherent pill(s). If a pill is grabbed by the orifice, after the suction probe moves, the pill(s) grabbed by the orifice are released to drop back into the bulk container.

The optional iterative process of FIG. 22 will "measure" the length of the pill so as to essentially "cut off" any potential hanging pills as a result of adhesion, which may be characterized by the nature or type of the medicament (1105). This process is necessary if the long dimension of the pill is not known. If the long dimension of the pill is reliably known, this process can be skipped or implemented for confirmation. In step 1110 the orifice remains at the optimum setting previously derived from the first sizing process and, as before, the retrieval probe is extended downward into the container as one or more pills are secured and lifted through the orifice. Block 1120 interjects a delay factor, based on the known probe vertical speed, which serves as a "time out" to provide for passage of the primary pill and identify the most probable timing for the engagement of the adhering pill by rapidly constricting the orifice in step 1130. Alternatively, an iterative process adjusting the vertical translation distance of the retrieval probe can be used.

The time delay is initially derived from the linear speed of the probe and thus pill and can be measured in cm/sec. For example, if a pill has a vertical dimension of 1.5 cm (not known a priori) and the probe moves at a rate of 6 cm/sec, the baseline delay before constricting the orifice would be 250 msec. from the leading edge of the primary pill (which corresponds to the probe tip surface. As will be appreciated, the distance is controlled as a function of the relative relationship between the probe and the aperture, and may also be done by vertical position translation in increments.

In the case where the orifice is allowed to completely close, as in decision block 1135, it is assumed that the orifice either closed just before (neatly pinching the tandem adhered pill off) or after the tandem pill passed, or in the alternative because there were no "dangling" pills present. Considering that it is intended to have the orifice close against the pill, the baseline delay in step 1125 is adjusted with a positive off-set until the orifice is not able to fully close due to the trapping of an additional pill within the variable orifice. In the alternative, it is contemplated that in the absence of a tandem pill the orifice would be closed immediately after the trailing edge of the primary pill has passed through the orifice. Accordingly, in the first case the delay in step 1025 would be substantially equal to the time it takes to move from the leading edge of the first pill to approximately the middle of the following pill or in the second case the orifice is constricted just after the trailing edge of the first pill and prior to the leading edge of the hanging tandem pill(s). Step 1145, similar to step 1040, further serves as a verification block whereby reiterative steps are performed to ensure that tandem pills are being excised correctly. The anti-adhesion delay constant is subsequently stored in system memory in order to be referenced during subsequent acquisitions of pills or objects from that bulk container, and lastly step 1150 places the dispenser back in normal operation. If pills are grabbed (determined by the orifice not able to completely close (using a force or similar sensor to assess) then that vertical excursion distance is noted (e.g., steps 1130-1135). An iterative process can be used to learn the vertical excursion height that only allows one pill to get through the orifice. This height can be assessed such that the pill needs to be 'grabbed' in a particular orientation (e.g. a tablet needs to be grabbed on the flat side by the suction probe as opposed to the edge). The iterative process is more efficient if most pills do not have other adhered pills but can work as long as some pills are single and orient in the optimal orientation by the suction probe. This process can require multiple trials (e.g. 10 as indicated in step 1145). The reader will understand that during this iterative process to determine the minimal vertical height, the orifice can close onto the pill with the vertical probe stationary and then reopen without dislodging the pill, permitting the vertical probe to iteratively increment without having to retrieve another pill each time. At least one time only one pill will be picked up in the optimal orientation so the process will be able to identify one pill's minimal vertical excursion distance with set number (e.g. 10) iterations.

As indicated in FIG. 22, once a pill is engaged and retrieval starts, the system maintains the desired orifice size to permit a pill to pass through and then closes the orifice to assure that the second pill which may be adhering does not pass through. This may be done by a time delay as indicated in the flowchart or as a result of a distance sensing through the probe drive mechanism or a sensor responsive to the position of the probe. The iterative adjustment of the time delay at step 1125 will result in a single pill being passed while preventing any adhering pills from passing through the orifice. It is noted that the additional cycling of the orifice mechanism, both in the "calibration" cycle as well as in operation when the anti-adhesion process is invoked, could result in increased wear on the orifice's internal edge and the size control mechanisms, such that appropriate materials and/or coating may be used to provide wear resistance and reliable operation of the apparatus.

Special circumstances may also be encountered in the disclosed system and methods and the following is a general discussion of several of such circumstances. For example, if the orifice size needed in the retrieval process is smaller than the probe diameter, then the orifice can be set wide enough to allow the probe to pass and then closed to appropriate size just after the tip of probe passes through the orifice. The probe can stop vertical movement when its tip is just above the top of the narrowest portion of the orifice to allow the orifice size to be set to a smaller, appropriate, size.

Typically, if the orifice is set at less than two times the middle diameter of the object being retrieved and closing the orifice at less than twice the longest diameter will guarantee that only one pill is removed at a time. An exception may be for pills with similar middle and longest diameter (e.g. round tablets). In such a circumstance, closing the orifice after vertical movement of the probe at less than two times the smallest diameter will guarantee one pill is removed. In practice, since the orifice in the system may have rounded edges, the maximal orifice size can be set to equal to or less than 1.5 (instead of 2) as long as pills are symmetrically beveled on edges (or at least not sloped from one edge to more than one half the way to the other edge) to guarantee pill separation. It is further contemplated that alternative shapes for the orifice may further optimize the ability of the system to assure singulation of oddly-shaped objects.

As noted above, once the "calibration" operations have been completed and the settings are determined for a specific type of pill in a container, those settings are stored in the system database (memory) and are associated with that pill and container and used subsequently each time a pill is called for from that container.

Although two mechanical singulation embodiments are described in detail, the reader should appreciate that other variable orifice embodiments are possible including a nut and hollow screw with longitudinal flutes and flexible prongs, where the adjustment of the position of the nut relative to the screw results in the movement of the flutes and prongs, thereby controlling the size of the orifice. Moreover, any radially oriented elastic or contractile elements (such as a biological eye iris), etc. may be employed for the orifice and it will be appreciated that the orifice should be adjustable so as to provide the functionality described above and in more detail below. It should also be appreciated that the variable orifice disclosed herein can be used with a variety of other object retrieval systems to provide for object singulation as well.

As an alternative embodiment to the pre-dispense receptacle and restocking container, also contemplated is the use of a plurality of pre-dispense receptacles suspended above each of the pill containers (220, 224) as carousal 210 rotates. Once a pill is reliably retrieved it is placed into pre-dispense receptacle until such time as dispensing occurs. As mentioned previously, if the individual pills have not been dispensed in a designated time they may be gravity fed back into their respective storage container (below the pre-dispense container) for future dispensing. Such an embodiment, while requiring additional movement and/or hardware to provide a pre-dispense receptacle for each container or bin, may reduce or eliminate the need to restock missed medication dosages.

As noted previously the dispensing device can be enclosed within a housing that is lockable so as to be accessible only with a key or combination, such that the medicaments may be isolated from environmental exposure, especially to humidity. A replaceable desiccant can also be included within this compartment, as well as other components that may be needed to control or modify the environment in which the medicaments or other objects are stored. For example, the compartment can be opaque to prevent light exposure. Light, humidity, and temperature sensors can be included to assess for environmental alterations that may affect pill stability and shorten the time to expiration date. Another example of an environment modifying component would be a cooling unit included in certain circumstances to regulate temperature.

The embodiments above also can include a device or mechanism for "listening" to or otherwise monitoring the retrieval process. Such a device can include a piezoelectric/pressure plate (essentially a counter/sorter). For example, if a vacuum probe drops a pill or pills onto a pressure plate that could be detected. Similarly, the system may be able to detect that one pill has been deposited into the pre-dispense receptacle, or if the system detects two or more pills, or is equivocal, the pills can be set aside for restocking and the retrieval process repeated.

Figure 20:
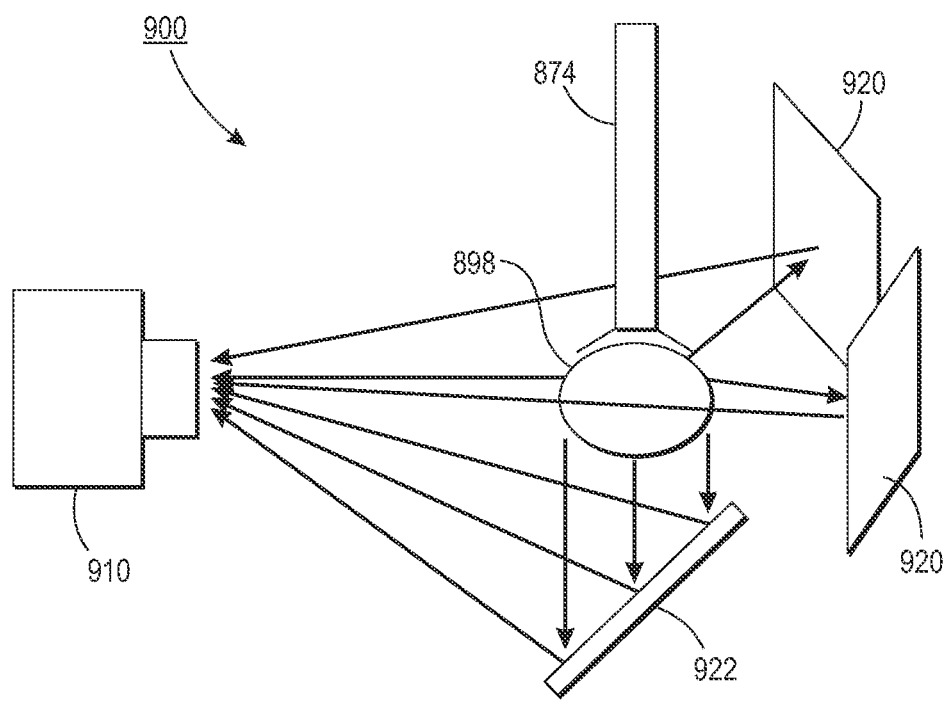
FIG. 20 is a general illustration of an exemplary image capture apparatus in accordance with an aspect of the disclosed embodiments.

Turning to FIG. 20, an imaging system 900 is depicted to enable image identification of an object. In the embodiment of a medication dispenser described above, one example of such an imaging system was described relative to FIGS. 8 and 10C, for example. The imaging system can be placed in the region where the suction probe traverses the pill from the bulk container (after passing through the variable orifice as described above) to the temporary or pre-dispense receptacle. In this region a specific location can be designated as the imaging location where the probe, with gripped pill, can briefly pause for image capture. The designated imaging location is most likely when the pill gripped by the probe tip is in the location depicted. In this location a digital camera 910 or similar imaging device can be placed and focused for optimal imaging. As suggested herein, the system may include an image database, stored in memory, which includes images and characteristic data for a plurality of objects (e.g., pills), and where a processor such as the microcontroller operates to compare the plurality of images that were captured against data stored in the image database to determine a match between the object and an entry in the database in order to determine a characteristic of and to identify the object.

Also contemplated is the use of an imaging system employing a camera (e.g., 480, 910) as a singulator, where the digital image capture apparatus and associated image processing circuitry analyze images of a retrieved object(s) to determine whether a single object has been retrieved. As described above, an image-based singulation apparatus may further enable the characterization and/or verification of the object type to assure that an appropriate medication (e.g., pill type) has been retrieved for dispensing. Furthermore, the use of a plurality of singulation techniques, such as image-based and variable aperture singulation in combination, is also contemplated. For example, the image-based singulation could serve as a "check" to confirm that only a single object is retained on the retrieval probe after the probe is retracted through the variable orifice.

As will be apparent in the following disclosure, imaging of multiple sides of the pill can also be performed to obtain adequate information for pill identification. The data from the images (obtained with digital imaging methods) can be processed by a variety of algorithms, well known in the field, to extract features of the object (pill) such as shape, size, color, and markings. Optical character recognition algorithms can also be used to identify the specific markings on the pills. The camera characteristics, for instance distance from object, will be known to aid in the feature extraction. The extracted features can then be compared and matched to a database resident in the system memory to identify the specific object, which in the case of a pill will include the specific medication, dose size, and manufacturer (mainly useful in the case where there are generic versions of the medication). In the event a match cannot be made confidently with a computerized algorithm, the images can be provided to a caregiver or specialist (e.g. pharmacist or physician using remote communication) and the pills can be manually identified.

The pill identification techniques can also be used to confirm that the appropriate medication was loaded into the bulk compartment. The process may be run after loading the medication yet prior to dispensing, and may be completed by imaging of the pills in a bin or container, as described above, or with each pill designated for dispensing (i.e. gripped by the probe and being transferred from the bulk to temporary storage container) or with some, but not all, of the pills designated for dispensing. If an incorrect pill is identified, it can indicate that the bulk container was loaded with the incorrect pills or a mixture of pills is present. The system can be programmed not to dispense incorrect pills and to require that the bulk container be removed, emptied and that the appropriate medication be reloaded.

In one imaging embodiment multiple cameras can be positioned to image various sides of the pill or other features or components of the system (e.g., pre-dispense receptacle, dispense cup, etc. Also contemplated is the use of mirrors in the image are of a camera that are convex, providing for the possibility of more detailed resolution in the reflected pill images. A variety and combination of mirror geometries can be used as long as the surface and reflection have known mathematical properties that can be used to correct for the distortions in the acquired images and the image processing feature extraction methods. With respect to FIG. 21, the figure depicts a side view of an embodiment with mirrors located in different imaging planes including one located below the probe to view the bottom surface of the pill. The bottom mirror 922 will be particularly important for imaging tablet shaped pills that are gripped by the probe on the broad surface. In this case, only one of the broad sides will be imaged (bottom) because the other broad side (top) is adhered to the probe. The initial pill identification process after bulk loading can require repeated retrieval, imaging, restocking steps to assure that with reasonable certainty, both sides of the pill are imaged for identification. This is especially relevant if the images of one side of the tablet are not adequate to provide for pill identification.

The lighting necessary for adequate imaging is a significant consideration. Different types of lighting can result in images that provide more information for a particular feature extraction. A diffuse light can provide for better shape, size and color determination, whereas a grazing or transverse light can provide for better marking extraction especially for markings that consist of impressions or elevations. Thus, multiple lights with different characteristics (not shown) can be used to optimize the images, and several images in each position with different lighting can be used to provide for adequate/optimal images for feature extraction and pill identification.

As another alternative to multiple cameras or mirrors, the camera can be moved around the pill to provide for complete imaging of the exposed surface. Alternatively, a strategically placed mirror that rotates or is otherwise moved can be used to capture images of the various sides of the pill. Also contemplated is that the probe gripping the pill can change orientation, for example partially rotate to provide for partial or complete imaging of the exposed pill surface. Further contemplated are external lens between the camera and pill or another object. The camera can have internal lens(es) and focusing mechanisms as well as or other optical systems such as prisms including complex prisms (for example pentaprisms and roof pentaprisms) and partially mirrored surfaces can be placed between the object and camera to optimize the images and/or collect multiple perspectives in a single image. The optical systems can permit imaging through a range of distances and geometries with the same camera. Known characteristics of the interposed optical systems can be used by the various algorithms to construct and analyze the captured images.

Imaging of different device components can have different purposes. For example, images of the container can be used to determine if pills (or other objects) remain in the container or if the container is empty; images of the pre-discharge receptacle can be used to confirm that the receptacle appropriately emptied during the dispense or restock steps; imaging of the dispense cup can be used to confirm all of the pills (or other objects) were dispensed and that the dispense cup is returned into the device by the user empty. All of these images can be saved in local or remote storage systems in perpetuity for subsequent use or review.

It should be apparent to the reader that a combination of the above methods or similar methods can be used to provide for adequate/optimal imaging of the pill surface in the dispenser to optimize identification of the pill. It should also be apparent, that the imaging system can be used to identify if more than one pill is gripped by the probe or if a pill fragment is gripped by the probe. Additionally it should be apparent that the imaging system can be used to image other components of the device such as the various containers to determine if any of the containers is empty or has pills within it.

In summary, a dispensing system is disclosed comprising a programmable, on-site dispensing unit having a singulator to assure only a single object is allowed to be retrieved at one time. In one embodiment as an in-home medication dispensing unit the system holds medication in a plurality of bulk containers whereby a retrieval probe retrieves a pill according to a programmed prescription regimen and deposits the pill into the intermediate or pre-dispense storage container. When the patient responds to an indicator (alarm, light, etc.) by actuating a switch within a specified time, the unit administers the pills that have previously been retrieved and staged for dispensing. If the patient fails to respond within the specified time, the medication is returned to a restocking container and a message may be sent to a remote location (e.g., to a designated care giver or a central monitoring facility). Notably, in several embodiments a variable orifice may be used for singulation, where the orifice size is not only adjustable or variable to fit a wide range of objects, but it may be employed in a dynamic manner to not only "calibrate" itself to assure singulation of the objects being retrieved, but to further assist with such singulation by using the variable orifice in a clamp-like fashion. In combination with various methods the variable orifice significantly improves the reliability of extracting only a single pill at a time for controlled dispensing. Additionally, an imaging system can be included to permit image identification and/or confirmation of the specific objects, as well as to provide an aid to assure object singulation.

It will be appreciated that various above-disclosed embodiments and other features and functions, or alternatives thereof, may be desirably combined into many other different systems or applications. Also, various presently unforeseen or unanticipated alternatives, modifications, variations or improvements therein may be subsequently made by those skilled in the art which are also intended to be encompassed by the following claims.

What is claimed is:

1. An object dispensing system, including:
    a housing comprising a rotatable carousel below a support frame, the rotatable carousel including a plurality of individually removable containers where each container provides a repository for objects therein;
    an access port in the support frame of the housing through which an object may be removed from each of the plurality of containers, in seriatim;
    a pre-dispense port in the support frame of the housing providing controlled access to one of a plurality of output containers; and
    a retrieval probe, said probe located within the confines of the housing and operatively sliding between the access port and the pre-dispense port, said probe including a compliant tip for releasably engaging an object in one of the plurality of containers via said access port, said probe retrieving the object from a container and then moving between the access port and the pre-dispense port to deliver the object to a dispensing receptacle via the pre-dispense port further comprising: a controller; a carousel rotation drive for causing the rotation of the carousel under the programmatic control of the controller; a retrieval probe slide motor, for causing the movement the sliding of the retrieval probe slide in a horizontal direction over the access port under the programmatic control of the controller; a vertical slide motor operatively associated with the retrieval probe to control the vertical position of the retrieval probe under the programmatic control of the controller; wherein the controller operates to alter the relative position between the retrieval probe and the container beneath the access port, thereby enabling the retrieval probe to attempt to retrieve an object from a plurality of horizontally spaced locations within a container.

2. The object dispensing system according to claim 1, further including a singulator, operatively interposed adjacent the access port, said singulator operating to assure that only a single item is removed at a time by the retrieval probe.

3. The object dispensing system according to claim 2, wherein said singulator includes at least one imaging device and a plurality of mirrors to view an object retrieved by the retrieval probe while above the access port, whereby output of the imaging device is analyzed and in the event more than one object is suspended from the compliant tip, the objects will be released.

4. The object dispensing system according to claim 3, wherein said imaging device captures at plurality of images of the object, said system further comprising:
    an image database, stored in memory, said database including images and characteristic data for a plurality of objects;
    a processor operatively connected to the image database, said processor being suitable for comparing the plurality of images against data stored in the image database to determine a match between the object and an entry in the database in order to determine a characteristic of the object.

5. The object dispensing system according to claim 1, wherein said singulator includes at least one variable orifice through which the compliant tip of the retrieval probe may pass, said variable orifice being capable of adjustment to singulate the object suspended from the compliant tip as the tip is withdrawn from the container and thereby prevent the removal of more than one object at a time from the container.

6. The object dispensing system according to claim 1, wherein each of said removable containers is an open-top container.

7. The object dispensing system according to claim 6, further comprising:
    a first movable cover associated with both the access port and pre-dispense port; and
    a second movable cover associated with each of the plurality of containers supported by the carousel, wherein the first and second movable covers are operatively engaged to seal the containers and access port and prevent an object from being removed from the container when the system is not in operation.

8. The object dispensing system according to claim 7, wherein a single mechanism is employed to coincidently control the engagement and disengagement of both the first and second covers.

9. The object dispensing system according to claim 1, further comprising a processor operatively associated with the housing, said processor controlling the operation of the carousel and the retrieval probe to assure that an object in a selected container is retrieved and dispensed by the system.

10. The object dispensing system according to claim 1, further comprising:
    a re-stock receptacle to receive any non-dispensed items, said restock receptacle storing the items until a manual intervention results in the items being restocked in an appropriate bin; and a database, stored in memory, for tracking those items that are placed into the restock bin and decrementing the items from a supply of available items, also reflected in the database, until such time as the items are restocked into a respective container.

11. The object dispensing system according to claim 1 wherein said retrieval probe is hollow and is connected to a controllable vacuum source to provide a vacuum tip at one end that releasably engages the object for removal from the container using the vacuum to attach the object.

12. The object dispensing system of claim 3, wherein said probe retracts upon drawing a vacuum at the tip by contacting at least one object.

13. A medicament dispensing method comprising:
providing a dispensing system, including a housing having a rotatable carousel therein with a plurality of removable open-top containers, where the carousel moves under the control of a carousel drive, each open-top container including a repository for objects therein; an access port in the housing through which an object may be removed from the plurality of open-top containers, in seriatim; a pre-dispense port in the housing providing controlled access to at least one output container; and a retrieval probe, said probe located within the housing and operatively movable under the control of a horizontal slide drive by a slide motor between the access port and the pre-dispense port, said probe further including a vertical slide retracting and extending the probe and a compliant tip thereon under control of a vertical slide motor, the probe tip releasably engaging an object in one of the plurality of open-top containers via the access port,
placing a different medicament into at least two of the plurality of containers;
in response to a dispense request, a controller operating to move the carousel to place an open-top container having the requested medicament beneath the access port, and moving the horizontal probe slide into a position so that the probe tip is over the access port, wherein the probe is then extended to engage a medicament, and once engaged by the probe tip, the medicament is raised while attached to the probe tip and retrieved from the open-top container via the access port;
said controller then engaging the horizontal slide drive to cause the horizontal probe slide to move into a position over the pre-dispense port;
releasing the medicament from the probe tip to deliver the medicament to a pre-dispense receptacle beneath the pre-dispense port; and
moving the pre-dispense receptacle, using a pre-dispense slide motor responsive to the controller, to transfer the medicament from the pre-dispense receptacle to a dispense cup accessible by a user.

14. The medicament dispensing method according to claim 13, further comprising:
providing a first sliding cover that moves between an open position that permits access to the access port and the pre-dispense port, and a closed position that covers both ports; and
providing a container cover that is suitable for covering the top surface of the containers except beneath both ports, wherein the container cover employs a cam-operated mechanism to raise the cover to an open position permitting rotation of the containers on the carousel or lower the cover to a position in general contact with the top edges of containers on the carousel;
wherein the first sliding cover is operatively attached to the container cover such that movement of the sliding cover between the open and closed positions similarly moves the container cover between the raised and lowered position, and where a cover motor, operatively attached to the first sliding cover through at least one linkage, causes the first sliding cover to move in response to signals generated from the controller.

15. The medicament dispensing method according to claim 13, further comprising singulating the medicament attached to the end of the probe upon retrieval via the access port to assure that only one object is retrieved.

16. The medicament dispensing method according to claim 13, further comprising applying a vacuum pressure to the probe tip, said vacuum pressure causing an attraction between the probe tip and the medicament, and sensing the pressure at the probe tip to monitor the status of the medicament attachéto the tip, wherein a loss of vacuum is indicative that the medicament is no longer attached.

17. The medicament dispensing method according to claim 13, further comprising causing a relative movement between the probe and a container by causing a slight movement of at least one of the carousel and the horizontal slide to change the position in the container into which the probe is extended.

18. A medicament dispensing system, comprising:
a housing comprising a rotatable carousel below a support frame, the rotatable carousel including a plurality of open-top, removable containers where each open-top, removable container provides a repository for medicaments therein;
an access port in the support frame of the housing through which an object may be removed from each of the plurality of open-top, removable containers, in seriatim;
a pre-dispense port in the support frame of the housing providing controlled access to one of a plurality of output containers;
a hollow retrieval probe connected to a controllable vacuum source to provide a vacuum tip at one end that releasably engages the medicament for removal from one of the open-top, removable containers using the vacuum to attach the medicament, wherein said probe retracts upon drawing a vacuum at the tip by contacting at least one medicament and where said probe located within the confines of the housing and operatively sliding between the access port and the pre-dispense port, said probe including a compliant tip for releasably engaging an medicament in one of the plurality of open-top, removable containers via said access port, said probe retrieving the medicament from an open-top, removable container and then sliding between the access port and the pre-dispense port to deliver the medicament to a dispensing receptacle;
a singulator, operatively interposed adjacent the access port, said singulator operating to assure that only a single medicament object is removed at a time by the retrieval probe, wherein the singulator is selected from the group consisting of an imaging capturing device; an iris-type variable orifice, and a variable orifice formed between a pair of rollers each having a cam-shaped recess thereon;
a first movable cover associated with both the access port and the pre-dispense port;

a second movable cover associated with each of the plurality of open-top, removable containers supported by the carousel, wherein the first and second movable covers are operatively engaged to seal the open-top, removable containers and access port and prevent an medicament from being removed from any open-top, removable container when the system is not in operation, wherein the first and second movable covers are operatively connected via a single mechanism employed to coincidently control the engagement and disengagement of both the first and second covers;

a processor enclosed within the housing, said processor controlling the operation of the carousel and the retrieval probe to assure that a medicament in a selected open-top, removable container is retrieved and dispensed by the system;

a re-stock receptacle to receive any non-dispensed items, said restock receptacle storing the items until a manual intervention results in the items being restocked in an appropriate bin;

a database, stored in memory, for tracking those items that are placed into the restock bin and decrementing the items from a supply of available items, also reflected in the database, until such time as the items are restocked into a respective open-top, removable container.

19. The medicament dispensing system according to claim 18, further comprising:
a controller;
a carousel rotation drive for causing the rotation of the carousel under the programmatic control of the controller;
a retrieval probe slide motor, for causing the movement of the retrieval probe slide in a horizontal direction over the access port under the programmatic control of the controller;
a vertical slide motor operatively associated with the retrieval probe to control the vertical position of the retrieval probe under the programmatic control of the controller; wherein the controller operates to alter the relative position between the retrieval probe and the open-top, removable container beneath the access port, thereby enabling the retrieval probe to attempt to retrieve a medicament from a plurality of horizontally spaced locations within a an open-top, removable container.

* * * * *